United States Patent [19]

Gutierrez et al.

[11] Patent Number: 4,906,394
[45] Date of Patent: Mar. 6, 1990

[54] LACTONE MODIFIED MONO-OR DICARBOXYLIC ACID BASED ADDUCT DISPERSANT COMPOSITIONS

[75] Inventors: Antonio Gutierrez, Mercerville; Robert D. Lundberg, Bridgewater, both of N.J.

[73] Assignee: Exxon Chemical Patents Inc., Linden, N.J.

[21] Appl. No.: 916,108

[22] Filed: Oct. 7, 1986

[51] Int. Cl.$^4$ ............................. C10M 133/16
[52] U.S. Cl. ......................... 252/51.5 A; 44/66; 44/73; 260/404.5; 560/155; 564/134; 564/141; 549/263
[58] Field of Search ............. 252/51.5 A; 44/66, 73; 260/404.5; 521/140; 525/186, 190; 560/1, 155; 564/134, 141; 549/263

[56] References Cited

U.S. PATENT DOCUMENTS

| | | | |
|---|---|---|---|
| Re. 26,330 | 1/1968 | Colfer | 208/48 |
| 2,290,154 | 7/1942 | Blair, Jr. | 252/344 |
| 2,409,275 | 8/1956 | Harris | 260/404.5 |
| 2,568,619 | 9/1951 | Gregory | 260/484 |
| 2,638,449 | 5/1953 | White et al. | 252/51.5 |
| 2,759,894 | 8/1956 | Matuszak | 252/51.5 |
| 2,767,144 | 10/1956 | Gottshall et al. | 252/57 |
| 2,890,208 | 6/1959 | Young et al. | 260/78.3 |
| 3,025,323 | 3/1962 | Rose et al. | 260/561 |
| 3,062,631 | 11/1962 | Thompson | 44/71 |
| 3,087,936 | 4/1963 | Le Suer | 260/326.3 |
| 3,131,150 | 4/1964 | Stuart et al. | 252/34.7 |
| 3,154,560 | 10/1964 | Kirkwood | 260/326.3 |
| 3,169,945 | 2/1965 | Hostettler et al. | 260/78.3 |
| 3,172,892 | 3/1965 | Le Suer et al. | 260/326.5 |
| 3,198,736 | 8/1965 | Henderson | 252/46.7 |
| 3,202,678 | 8/1965 | Stuart et al. | 260/326.5 |
| 3,215,707 | 11/1965 | Rease et al. | 260/326.5 |
| 3,219,666 | 11/1965 | Norman et al. | 260/268 |
| 3,232,587 | 11/1966 | Rease et al. | 260/346.8 |
| 3,269,946 | 8/1966 | Wiese | 252/32.5 |
| 3,272,743 | 9/1966 | Le Suer | 252/32.5 |
| 3,272,746 | 9/1966 | Le Suer | 252/47.5 |
| 3,278,550 | 10/1966 | Le Suer | 260/326.3 |
| 3,284,409 | 11/1966 | Dorer | 252/49.9 |
| 3,284,417 | 11/1966 | Hostettler et al. | 260/78.3 |
| 3,288,714 | 11/1966 | Osuch | 252/57 |
| 3,325,484 | 6/1967 | Deghenghi et al. | 260/239.55 |
| 3,341,458 | 9/1967 | Mayhew et al. | 252/117 |
| 3,361,673 | 1/1968 | Stuart et al. | 252/51.5 |
| 3,367,895 | 2/1968 | Clark | 260/22 |
| 3,379,693 | 4/1968 | Hostettler et al. | 260/77.5 |
| 3,381,022 | 4/1968 | Le Suer | 260/404.5 |
| 3,390,086 | 6/1968 | O'Halloran | 252/47.5 |
| 3,401,118 | 9/1968 | Benoit et al. | 252/51.5 |
| 3,403,102 | 9/1968 | Le Suer | 252/49.8 |
| 3,424,771 | 1/1969 | Libby et al. | 260/404.5 |
| 3,436,463 | 4/1969 | Mayhew et al. | 424/320 |
| 3,438,943 | 4/1969 | Miranda et al. | 260/75 |
| 3,455,827 | 7/1969 | Mehmedbasich et al. | 252/32.7 |
| 3,483,145 | 12/1969 | Levy et al. | 260/2 |
| 3,493,568 | 2/1970 | Levy et al. | 260/244 |
| 3,522,179 | 7/1970 | Le Suer | 252/51.5 |
| 3,562,159 | 2/1971 | Masten | 252/32.7 |
| 3,576,743 | 4/1971 | Widmer et al. | 252/51.5 |
| 3,632,510 | 1/1972 | Le Suer | 252/35 |
| 3,684,771 | 8/1972 | Braun | 260/77 |
| 3,699,165 | 10/1972 | Albers et al. | 260/561 B |
| 3,708,522 | 1/1973 | Le Suer | 260/485 G |
| 3,779,724 | 12/1973 | Kerschner et al. | 44/71 |
| 3,792,061 | 2/1974 | Zecher et al. | 260/326 N |
| 3,799,877 | 3/1974 | Nnadi et al. | 252/51.5 R |
| 3,836,470 | 9/1974 | Miller | 252/51.5 A |
| 3,836,471 | 9/1974 | Miller | 252/51.5 A |
| 3,838,050 | 9/1974 | Miller | 252/40.5 |
| 3,838,052 | 9/1974 | Miller | 252/56 R |
| 3,879,308 | 4/1975 | Miller | 252/56 R |
| 3,894,849 | 7/1975 | Polss | 44/66 |
| 3,912,764 | 10/1975 | Palmer | 260/346.8 |
| 3,927,041 | 12/1975 | Cengle et al. | 260/346.8 |
| 3,950,341 | 4/1976 | Okamoto et al. | 252/32.7 E |
| 3,997,569 | 12/1976 | Powell | 44/63 |
| 4,017,406 | 4/1977 | Brois et al. | 252/51.5 A |
| 4,062,786 | 12/1977 | Brois et al. | 252/51.5 R |
| 4,086,294 | 4/1978 | Koleske et al. | 260/834 |
| 4,102,798 | 7/1978 | Ryer et al. | 252/51.5 A |
| 4,110,349 | 9/1978 | Buckler et al. | 260/346.74 |
| 4,113,639 | 9/1978 | Lonstrup et al. | 252/51.5 A |
| 4,116,875 | 9/1978 | Nnadi et al. | 252/49.7 |
| 4,116,876 | 9/1978 | Brois et al. | 252/49.6 |
| 4,123,373 | 10/1978 | Brois et al. | 252/48.6 |
| 4,132,531 | 1/1979 | Cummings et al. | 44/71 |
| 4,151,173 | 3/1979 | Vogel | 260/326.5 F |
| 4,169,836 | 10/1979 | Ryer et al. | 548/238 |
| 4,176,073 | 11/1979 | Ryer et al. | 252/32.7 E |
| 4,234,435 | 11/1980 | Meinhardt et al. | 252/51.5 A |
| 4,247,671 | 1/1981 | Reitz et al. | 526/260 |
| 4,261,871 | 4/1981 | Smith et al. | 260/18 EP |
| 4,263,014 | 4/1981 | Daves et al. | 44/63 |
| 4,263,153 | 4/1981 | Daves et al. | 252/47.5 |
| 4,292,184 | 9/1981 | Brois et al. | 252/46.3 |
| 4,292,187 | 9/1981 | Hentschel et al. | 252/49.5 |
| 4,362,635 | 12/1982 | Dhein et al. | 252/56 S |
| 4,379,914 | 4/1983 | Lundberg | 528/354 |

(List continued on next page.)

FOREIGN PATENT DOCUMENTS 00202024 11/1986 European Pat. Off. ........ 252/51.5 A
1054370 1/1967 United Kingdom .

Primary Examiner—Jacqueline V. Howard
Assistant Examiner—Margaret B. Medley
Attorney, Agent, or Firm—J. B. Murray, Jr.

[57] ABSTRACT

$C_5-C_9$ lactone based adduct materials are made by reacting a $C_5-C_9$ lactone with a polyamine, a polyol or an amino alcohol to form a lactone adduct intermediate, and thereafter reacting the intermediate with an aliphatic hydrocarbyl saturated or unsaturated, straight chain or branched chain monocarboxylic or dicarboxylic acylating agent having from about one to about 165 total carbon atoms in said straight or branched chain to insure that the resulting lactone adduct is hydrocarbon soluble. The resulting adduct material are useful per se, as oil soluble dispersant additives, and are useful in fuel and lubricating oil compositions including concentrates containing the additives.

78 Claims, No Drawings

U.S. PATENT DOCUMENTS

| | | | |
|---|---|---|---|
| 4,388,471 | 6/1983 | Wollenberg | 549/255 |
| 4,397,750 | 8/1983 | Chibnik | 252/51.5 A |
| 4,415,728 | 11/1983 | Tremblay | 528/279 |
| 4,448,905 | 5/1984 | Lin et al. | 521/184 |
| 4,450,281 | 5/1984 | Wollenberg | 549/255 |
| 4,463,168 | 7/1984 | Lundberg | 528/355 |
| 4,486,326 | 12/1984 | Guitierrez et al. | 252/49.7 |
| 4,502,970 | 3/1985 | Schetelich et al. | 252/32.7 E |
| 4,517,104 | 5/1985 | Bloch et al. | 252/49.5 |
| 4,532,058 | 7/1985 | Chafetz | 252/56.5 |
| 4,536,547 | 8/1985 | Lundberg et al. | 528/354 |
| 4,540,809 | 9/1985 | Yokoshima et al. | 549/255 |
| 4,584,117 | 4/1986 | Wollenberg | 252/51.5 A |
| 4,585,566 | 4/1986 | Wollenberg | 528/279 |
| 4,612,132 | 9/1986 | Wollenberg | 521/184 |
| 4,614,603 | 9/1986 | Wollenberg | 549/255 |
| 4,617,138 | 10/1986 | Wollenberg | 528/355 |
| 4,624,681 | 11/1986 | Wollenberg | 252/49.7 |
| 4,645,515 | 2/1987 | Wollenberg | 44/63 |
| 4,647,390 | 3/1987 | Buckley III et al. | 252/51.5 |
| 4,663,062 | 5/1987 | Wollenberg | 252/47.5 |
| 4,666,459 | 5/1987 | Wollenberg | 44/56 |
| 4,666,460 | 5/1987 | Wollenberg | 44/63 |
| 4,668,246 | 5/1987 | Wollenberg | 44/63 |
| 4,680,129 | 7/1987 | Plavac | 252/51.5 A |
| 4,741,848 | 5/1988 | Koch et al. | 252/49.6 |
| 4,820,432 | 4/1989 | Lundberg et al. | 252/51.5 A |
| 4,828,742 | 5/1989 | Lundberg et al. | 252/51.5 R |

LACTONE MODIFIED MONO-OR DICARBOXYLIC ACID BASED ADDUCT DISPERSANT COMPOSITIONS

RELATED U.S. APPLICATIONS

This application is related to the following applications filed by the inventors herein: Ser. No. 06/916,218; 10/7/86; now pending, Ser. No. 06/916,114 filed 10/7/86, now U.S. Pat. No. 4,866,139, Ser. No. 06/916,113 filed 10/7/86, now U.S. Pat. No. 4,866,140, Ser. No. 06/916,287, filed 10/7/86, now U.S. Pat. No. 4,866,135, Ser. No. 06/916/303 filed 10/7/86 now U.S. Pat. No. 4,866,142 and Ser. No. 06/916,217, filed 10/7/86, now U.S. Pat. No. 4,866,141. All of the above applications were filed on even date herewith. All of these related applications are expressly incorporated herein by reference in their entirety.

BACKGROUND OF THE INVENTION

1. Field of the Invention

This invention relates to oil soluble dispersant additives useful in fuel and lubricating oil compositions, including concentrates containing said additives, and methods for their manufacture and use. The dispersant additives are poly ($C_5$–$C_9$ lactone) adducts which have been prepared by first reacting a $C_5$–$C_9$ lactone with a polyamine, a polyol or an amino alcohol to form an intermediate adduct, whereafter the intermediate adduct is reacted with an aliphatic hydrocarbyl monocarboxylic or dicarboxylic acylating agent having from about 1 to about 165 total carbon atoms. The acylating agent can be saturated or unsaturated, branched chain or straight chain, and should contain at least about twelve carbon atoms in the chain to insure that the resulting dispersant additives are hydrocarbon soluble.

2. Prior Art

Carboxylic acid and anhydride adducts with polyols and polyamines are well known lubricating additives. These agents act to keep sludge and varnish dispersed in engine oils and have been very successful commercially.

It is also known that polymers of 6 to 10 membered lactones such as valerolactone or epsiloncaprolactone (hereinafter caprolactone or E-caprolactone), can be prepared by reacting the lactone monomer with a hydoxyl or amine initiator. When reacting E-caprolactone, for example, the polymerization reaction may be illustrated by the following equations:

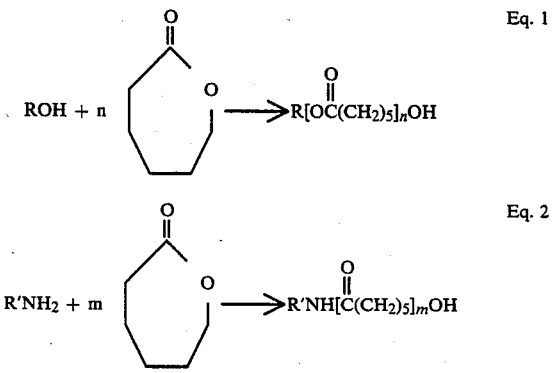

The reactions are known to be catalyzed by various esterification catalysts such as stannous octanoate, and a variety of different molecular weight products are feasible depending upon the ratio of lactone to initiator. Molecular weights on the order of form a few hundred up to about 5000 are reproducably achievable.

Caprolactone can also be polymerized to a very high molecular weight, e.g., on the order of 100,000 or more. Typically such high molecular weight polymers do not employ initiators and preservation of functionality is not a requirement.

It is also known to react a lactone such as E-caprolactone with a polyol to form polyesters having terminal hydroxyl groups which are useful as plasticizers.

It has now been found that improved oil soluble dispersant additives, useful in fuel and lubricating oil compositions, including concentrates containing the additives, can be prepared by first reacting a 6 to 10 lactone with either a polyamine, a polyol or an amino alcohol to form an intermediate adduct, and then reacting the intermediate adduct with a carboxylic acylating agent which contains at least one alkyl, alkenyl or alkynyl group having 12 or more carbon atoms to insure hydrocarbon solubility.

There are a number of prior art disclosures relating to adducts of lactones and polyols and/or amino alcohols to polyalkenyl succinic acid or anhydride type dispersants, and to fatty acid derivative dispersants. Other prior art shows lactone polymerization reactions. In general, however, little or no prior art of direct pertinence appears to have surfaced in regard to the present dispersants. Exemplary of the patent literature which relates to lactone polymerization processes and/or to oil soluble dispersant additives are the following U.S. Patents: U.S. Pat. No. 4,362,635 discloses synthetic ester oils which are esterification products of monoalcohols and dicarboxylic acids or of polyhydric alcohols and monocarboxylic acids respectively, containing 5 to 45% by weight of units of hydroxycarboxylic acids obtained from aliphatic alcohols, aliphatic, cycloaliphatic or aromatic carboxylic acids, and lactones of aliphatic $C_5$–$C_{12}$ hydrocarboxylic acids. The synthetic ester oils are suitable for the preparation of lubricants and lubricant compositions.

U.S. Pat. No. 2,890,208 discloses a process for polymerizing lactones to form lactone polyesters that are useful as plasticizers.

U.S. Pat. No. 4,062,786 and its continuation-in-part (U.S. Pat. No. 4,292,184) disclose lactone oxazoline reaction products of hydrocarbon substituted lactone carboxylic acids such as polybutyl lactone carboxylic acid, with a 2,2-disubstituted-2-amino-1-alkanol such as tris-(hydroxymethyl) amino-methane (THAM). The reaction products and their derivatives are disclosed as being useful additives in oleaginous compositions such as sludge dispersants for lubricating oil.

U.S. Pat. No. 4,379,914 and its continuation-in-part (U.S. Pat No. 4,463,168) disclose the preparation of polycaprolactone polymers by reacting E-caprolactone with a diamine wherein one of the amine groups of the diamine is a tertiary amine and the other is a primary or secondary amine. The polycaprolactone polymers are disclosed as being useful for neutralizing certain sulfonic acid-containing polymers to form amine-neutralized, sulfonated derivatives which can be combined with an alkyl benzene sulfonic acid to give a surfactant which contains ester groups, hydroxyl groups and amine-neutralized sulfonate groups.

U.S. Pat. No. 3,169,945 discloses the preparation of lactone polyesters which are useful as plasticizers and as intermediates for preparing elastomers and foams. The polyesters can be prepared by reacting a lactone such a E-caprolactone with an initiator such as an alcohol, amine or amino alcohol. A similar disclosure is contained in U.S. Pat. No. 3,284,417.

U.S. Pat. No. 3,025,323 relates to a class of diols which are derived through the action of omega-lactones on the primary amine groups of monoalkanolamines and on the amine groups of primary diamines. The compounds disclosed in this patent are useful as intermediates in the synthesis of polymers and as softeners and sizes for paper, leather and other porous materials.

U.S. Pat. No. 3,436,463 discloses N-substituted-gamma hydroxycarboxylic acid amides which are useful as nematocides and insecticides. The compounds of this patent are prepared by reacting an organic primary amine with a lactone such as gamma-butyrolactone or gamma-valerolactone.

U.S. Pat. No. 4,532,058 discloses as a motor oil dispersant, a spirodilactone condensation product formed by heating alkenyl succinic anhydrides in the presence of a basic catalyst, and then heating the resulting bicyclic spirodilactone condensation product with a polyamine or polyamine alcohol. It should be emphasized that this patent describes the intermolecular decarboxylation of an alkenyl succinic anhydride at elevated temperatures to form a condensation product and carbon dioxide as a by-product. This prior art is not concerned with polymerizable lactones which are the subject of the instant invention.

U.S. Pat. No. 2,638,449 discloses lubricating oil additives derived from alkenyl succinic anhydride esters of hydroxy compounds containing fatty acid amide groups.

U.S. Pat. No. 4,540,809 discloses acrylate esters of dipentaerythritol caprolactone condensates. The esters are useful as vehicles for paints and can be hardened by ionizing radiation or thermal means.

U.S. Pat. No. 4,086,294 discloses water soluble polycaprolactone-epoxide adducts which are produced by reacting a polycaprolactone polyol, a diepoxide and an anhydride of a polycarboxylic acid, such as substituted or unsubstituted succinic anhydride. The polycaprolactone-epoxide adducts are useful in the preparation of aqueous coating compositions. Similar polycaprolactone-epoxide adducts are disclosed in U.S. Pat. No. 4,261,871.

U.S. Pat. No. 3,438,943 relates to polyesters which are derived from oxazoline polyols which are prepared by reacting an acid or acid derivative and a polyhydroxy amine such as THAM. In cases where the acid is a fatty acid, the oxazolines are used as lubricants. Condensation of the oxazoline alcohols and polycarboxylic acids, including fat derived acids, e.g., azealic, yield polyesters that are used in aqueous paints.

U.S. Pat. No. 4,397,750 teaches the preparation of hydroxy substituted pyrrolidone esters from butyrolactones and polyhydroxyamines. Corresponding hydroxyamide side-products are also disclosed. The disclosed esters are useful as additives for lubricants and fuels.

U.S. Pat. No. 4,247,671 discloses the preparation of oxazoline alcohols via the condensation of, for example, caprolactone with an appropriate amine, for example, 2-amino-2-methyl-1-propanol. The oxazoline alcohols can be used to prepare oxazoline-containing polymer coatings. Analogous adducts prepared from butyrolactone and monohydroxy amino alcohols are disclosed in U.S. Pat. No. 4,448,905.

U.S. Pat. No. 3,493,568 discloses diol amides prepared from caprolactone and a monohydroxy amino alcohol. The diol amides can be cyclodehydrated to form oxazolines and oxazines which can be polymerized to yield crosslinked polymeric structures.

U.S. Pat. No. 4,017,406 discloses ester derivatives of long chain dicarboxylic anhydrides such as octadecenyl and polyisobutenylsuccinic anhydrides and aldehyde/THAM adducts for use as additives for oleaginous compositions.

U.S. Pat. No. 3,062,631 discloses condensation products of a beta-lactone and a polyamine which are useful as oil additives.

U.S. Pat. No. 2,290,150 discloses the use of amides of polyamines such as tetraethylene pentamine as a demulsifier. The acylating agents which are used to prepare the amides of this patent include straight and branched chain, saturated and unsaturated fatty acids or derivatives thereof.

U.S. Pat. No. 3,424,771 discloses the reaction products of fatty acid acylated polyamines and butyrolactones for use as aids in detergent compositions.

U.S. Pat. No. 2,409,275 relates to lubricating oil additives derived from the reaction of an anhydride of an acetic acid ester of a hydroxy polycarboxylic acid, e.g., citric acid with a carboxylic acid, e.g., fatty acid partial amide of an alkylene polyamine.

U.S. Pat. No. 3,341,458 relates to a lime soap detergent derived from 2-p-dioxanone and acylated ethanol amines.

U.S. Pat. No. 3,894,849 discloses a motor fuel additive which is an acrylated polyalkylene polyamine.

U.S. Pat. No. 4,017,406 discloses lubricating oil additives of monocarboxyl fatty acid esters of aldehyde-THAM adducts.

U.S. Pat. No. 2,759,894 discloses ester-oxazolines of fatty acids which are useful as lubricating oil additives.

U.S. Pat. No. 3,483,145 discloses polyester monooxazolines used as a monomer in the preparation of polymers.

U.S. Pat. No. 4,263,014 discloses fuel compositions containing dimer acids admixed with lactone-imidazoline derivatives.

U.S. Pat. No. 4,415,728 discloses the preparation of caprolactone copolyester diols via copolymerization of caprolactone and an alkoxylated Empol dimer acid. The diols of this patent are used in the preparation of polyurethane binders.

U.S. Pat. No. 4,540,809 teaches UV curable acrylate esters of caprolactone-dipentaerythritol condensates.

U.S. Pat. No. 4,292,187 relates to a condensation products which are prepared from at least one aliphatic or cycloaliphatic polyol, at least one aliphatic saturated or unsaturated $C_6$–$C_{22}$ hydroxycarboxylic acid or lactone thereof, and at least one saturated or unsaturated $C_6$–$C_{24}$ monocarboxylic acid. The condensation products of this patent are useful as effective lubricants for the working of metals or for admixture with other lubricating oils and conventional additives.

U.S. Pat. No. 4,234,435 discloses as oil additives, polyalkylene substituted dicarboxylic acids derived from poly-alkylenes having $M_n$ of 1300 to 5,000 and containing at least 1.3 dicarboxylic acid groups per polyalkylene. In Example 34 of this patent, a polyisobutene-substituted succinic acylating agent is reacted with caprolactam in the presence of mineral oil and sodium hydroxide.

U.S. Pat. No. 3,381,022 relates to ester derivatives of substantially saturated polymerized olefin-substituted succinic acid wherein the polymerized olefin substituent contains at least about 50 aliphatic carbon atoms and host a molecular weight of about 700 to 5,000. The esters include the acidic esters, diesters, and metal salt esters wherein the ester moiety is derived from monohydric and polyhydric alcohols, phenols and naphthols. The ester derivatives are useful as additives in lubricating compositions, fuels, hydrocarbon oils and power transmission fluids. A related application, i.e., U.S. Pat. No. 3,522,179, relates to lubricating compositions comprising a major amount of a lubricating oil and a minor proportion of an ester derivative of a hydrocarbon-substituted succinic acid sufficient to improve the detergency of the lubricating composition. The ester derivatives are similar to those described in U.S. Pat. No. 3,381,022 and contain at least about 50 aliphatic carbon atoms. The hydrocarbons substituent may be derived from a polymerized lower monoolefin having a molecular weight of from about 700 to about 5000.

All of the above discussed patents are expressly incorporated herein by reference in their entirety.

Additional exemplary prior art disclosures, which are expressly incorporated herein by reference in their entirety are U.S. Pat. Nos. 2,290,154; 2,568,619; 2,767,144; 3,062,631; 3,087,936; 3,131,150; 3,154,560; 3,172,892; 3,198,736; 3,202,678; 3,215,707; 3,219,666; 3,231,587; 3,325,484; 3,269,946; 3,272,743; 3,272,746; 3,278,550; 3,284,409; 3,284,417; 3,288,714; 3,361,673; 3,367,895; 3,379,693; 3,390,086; 3,401,118; 3,403,102; 3,455,827; 3,562,159; 3,576,743; 3,632,510; 3,699,165; 3,684,771; 3,708,522; 3,792,061; 3,799,877; 3,836,470; 3,836,471; 3,838,050; 3,838,052; 3,879,308; 3,912,764; 3,927,041; 4,062,786; 4,102,798; 4,110,349; 4,113,639; 4,116,875; 4,116,876; 4,123,373; 4,151,173; 4,167,073; 4,169,836; 4,263,153; 4,292,184; 4,379,914; 4,463,168; 4,486,326; 4,502,970; 4,517,104; 4,532,058; 4,536,547 and Reissue 26,330.

SUMMARY OF THE INVENTION

Despite the efficacy of prior art dispersant and oleaginous compositions, there is a need for more efficient and less costly dispersants which can either perform better, or perform well at lower dispersant levels. Accordingly, it is a principal object of this invention to provide novel lactone adduct based dispersants which are effective, and readily prepared under typical dispersant manufacturing conditions.

Another object is to provide a novel class of poly ($C_5$–$C_9$ lactone) adduct dispersants.

Another object is to provide a process for preparing efficient dispersants by reacting a saturated or unsaturated, straight or branched chain natural or synthetic, aliphatic hydrocarbon monocarboxylic or dicarboxylic acylating agent having from about 1 to about 165 total carbon atoms and from about 1 to about 85 carbon atoms in the straight or branched chain with a lactone adduct formed by reacting a $C_5$–$C_9$ lactone with a polyamine, a polyol, an amino alcohol or a mixture thereof.

A further object is to provide lubricant compositions and concentrates containing the novel $C_5$–$C_9$ lactone based dispersants of this invention.

Yet another object is to provide a novel class of preferable oil soluble dispersants from fatty acid acylating agents which have at least one $C_{12}$ or higher straight or branched chain alkyl, alkenyl or alkynyl group in their structure and which are reactive with an intermediate adduct formed by reacting a $C_5$–$C_9$ lactone with a polyamine, a polyol, an amino alcohol, or a mixture thereof.

Still another object is to provide $C_5$–$C_9$ lactone-polyol adducts which have been post-reacted with a long chain fatty acid or dimer thereof, as well as lubricant composition and concentrates containing the post-reacted adducts.

Another object is to provide $C_5$–$C_9$ lactone-polyamine adducts which have been post-reacted with a long chain fatty acid or dimer thereof, as well as lubricant compositions and concentrates containing the post-reacted adducts.

Still another object is to provide $C_5$–$C_9$ lactone-amino alcohol adducts which have been post-reacted with, a long chain fatty acid or dimer thereof, as well as lubricant compositions and concentrates containing the post-reacted adducts.

Still another object is to provide metal complexes and post-treated derivatives, e.g., borated derivatives, of the $C_5$–$C_9$ lactone derived dispersants of this invention, as well as lubricant compositions and concentrates containing such post-treated derivatives.

The manner in which these and other objects can be achieved will be apparent from the detailed description of the invention which appears hereinbelow.

In one aspect of this invention, one or more of the above objects can be achieved by reacting a $C_5$–$C_9$ lactone with a polyamine to yield a hydroxyl terminated amide structure containing a sequence of methylene units between the hydroxyl and amide groups, and thereafter reacting the hydroxyl terminated amide structure with a saturated or unsaturated, straight or branched chain natural or synthetic, aliphatic hydrocarbon monocarboxlic or dicarboxylic acylating agent having from about 1 to about 165 total carbon atoms and from about 1 to about 185 carbon atoms in the straight or branched chain with a lactone adduct formed by reacting a $C_5$– $C_9$ lactone with a polyamine, a polyol, an amino alcohol or a mixture thereof.

In another aspect, one or more of the objects of this invention can be achieved by heating a $C_5$–$C_9$ lactone such as E-caprolactone at a temperature of at least about 30° C., and preferably from about 75° C. to about 180° C. with a polyamine, and then heating the resulting adduct with a saturated or unsaturated, straight or branched chain natural or synthetic, aliphatic hydrocarbon monocarboxylic or dicarboxylic acylating agent having from about 1 to about 165 total carbon atoms and from about 2 to about 85 carbon atoms in the straight or branched chain with a lactone adduct formed by reacting a $C_5$–$C_9$ lactone with a polyamine, a polyol, an amino alcohol or a mixture thereof; and, in a further aspect, one or more objects of this invention are achieved by providing acylated $C_5$–$C_9$ lactone adducts produced by such a process.

One or more objects of this invention can be illustrated in connection with the reaction between a $C_5$–$C_9$ lactone such as E-caprolactone and a polyamine such as tetraethylene pentamine (TEPA) to form a hydroxyl terminated amide structure containing a sequence of five methylene units between the hydroxyl unit and the amide, followed by the reaction between the hydroxyl terminated amide structure and a $C_{12}+$ alkyl carboxylic acid material or a $C_{12}$–$C_{18}$ fatty acid or dimer thereof to form a hydrocarbon soluble dispersant. This process can be characterized by the following Examples equations:

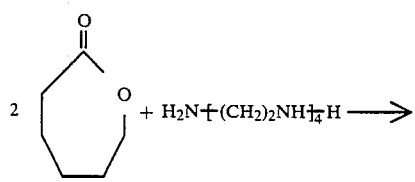 Eq. 3

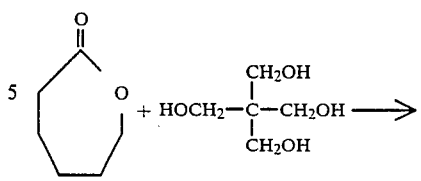 Eq. 5

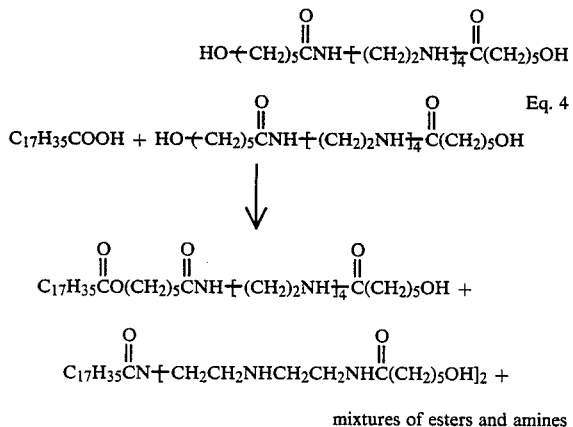 Eq. 4 mixtures of esters and amines

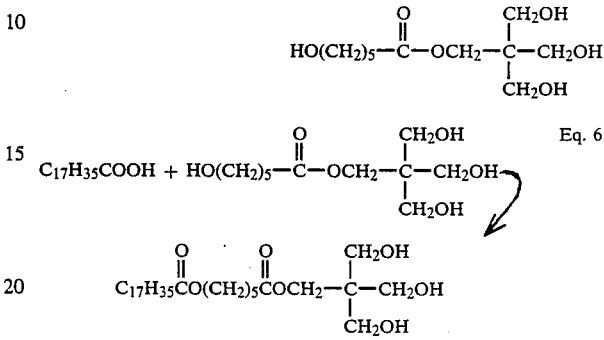 Eq. 6

Still other objects can be illustrated in connection with the reaction between E-caprolactone and a polyol such as pentaerythritol to form a polyol ester intermediate, which intermediate is then reacted with a long chain fatty acid or dimer thereof to form a fatty acid-polyol-caprolactone dispersant. This process can be characterized by the following general equations:

Still other objects can be illustrated in connection with the reaction between E-caprolactone and an amino alcohol such as 2-amino-2-(hydroxymethyl)-1,3-propanediol (THAM) to form a polyol amide which, upon heating, forms a hydroxyoxazoline intermediate. Either the polyol amide or the hydroxy-oxazoline intermediate can then be reacted with a long chain fatty acid or dimer thereof to form a hydrocarbon soluble dispersant. This process can be characterized by the following general equations:

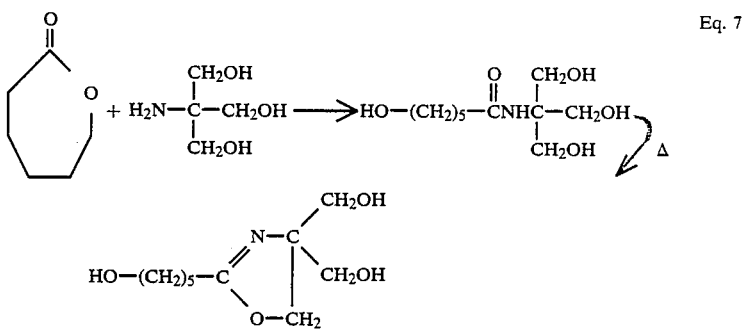 Eq. 7

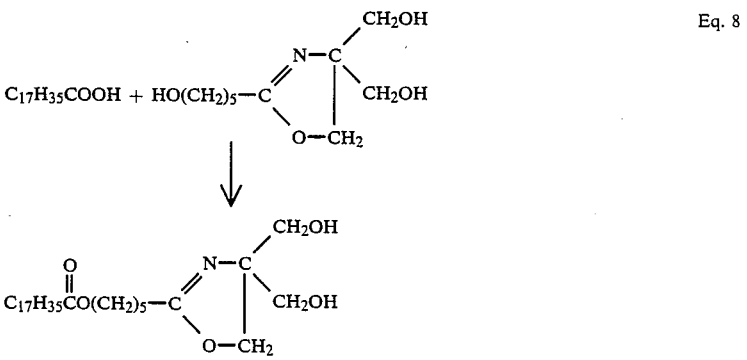 Eq. 8

The novel products of this invention are useful per se as an additive, e.g., a dispersant additive, for example, in the same manner as disclosed in U.S. Pat. No. 3,219,666 where prior art derivatives of polyalkenyl succinic acids and nitrogen compounds are used as dispersant/detergents in lubricants, especially lubricants intended for use in the crankcase of internal combustion engines, gears, and power transmitting units. Accordingly, one or more objects of this invention are achieved by providing lubricating oil compositions, e.g., automatic transmission fluids, heavy duty oils suitable for use in the crankcases of gasoline and diesel engines, etc. containing the novel $C_5$-$C_9$ lactone based products of this invention. Such lubricating oil compositions may contain additional additives such as viscosity index improvers, antioxidants, corrosion inhibitors, detergents, pour depressants, antiwear agents, etc.

Still further objects are achieved by providing concentrate compositions comprising from about 20 to about 80 weight % of a normally liquid, substantially inert, organic solvent/diluent, e.g., mineral lubricating oil, or other suitable solvent/diluent and from about 20 to about 80 weight % of a $C_5$-$C_9$ lactone based dispersant, as mentioned above and described in more detail hereinafter.

DESCRIPTION OF THE PREFERRED EMBODIMENTS

The Lactone Material

Useful lactone compounds for forming the intermediates or lactone adducts by reaction with a polyamine, polyol, or amino alcohol include lactones having at least five carbon atoms in the lactone ring, e.g., 5 to 9 carbon atoms. The lactone may be substituted or unsubstituted and the substituents, if any, may comprise, for example, alkyl, aryl, aralkyl, cycloalkyl, alkoxy or other which would not interfere with the ring opening reaction and adduct formation. The preferred lactones have no more than two substituent groups, and the more preferred lactones are unsubstituted.

Non-limited examples of the useful lactones include delta-valerolactone, methyl-delta-valero-lactone, E-caprolactone, methyl-E-caprolactone, dimethyl-E-caprolactone, methoxy-E-caprolactone, cyclohexyl-E-caprolactone, methylbenzyl-E-caprolactone, caprylolactone, methyl-caprylolactone, and the like, with E-caprolactone being particularly preferred.

REACTION OF THE LACTONE WITH A POLYAMINE

The above lactones such as E-caprolactone are cyclic esters which can be reacted with a polyamine to yield hydroxyl terminated amide adduct structure containing a sequence of methylene units between the hydroxy and the amide. In the case of E-caprolactone, which is a preferred lactone for use in this invention, the adduct contains a sequence of five methylene units between the hydroxyl and the amide groups. The stoichiometry of the lactone and polyamine determines the length of the polyester sequence in the resulting adducts as can be appreciated from Equation 3 above. Once these lactone-polyamine adducts are formed, reaction with an acylating agent such as an alkyl carboxylic acid material, e.g. octadecenyl succinic anhydride or a long chain fatty acid, e.g., isostearic acid, linoleic acid, oleic acid or dimers thereof, can be effected through the hydroxyl groups thereby forming an ester link with the acylating agent. The resulting materials, which are illustrated generally in Equation 4, display excellent bench test.

The chemistry of the lactone-polyamine reaction is such that primary amino functionality is more reactive than the secondary amino functionality in the polyamine structure and therefore the amide structure illustrated in Equation 3 will be the favored product. It is also possible, however, that the secondary amino functionality or the hydroxyl functionality of the resulting adducts can react with additional lactone molecules to form a diversity of structures.

In the reactions discussed above, the average degree of polymerization (DP) of the lactone monomer i.e., the sequence of lactone units in a row in the lactone adduct, may vary depending upon the intended application. At DP's of much greater than about 10 the dispersants formed from the lactone adducts can exhibit crystallinity; a characteristic which is undesirable in an oil soluble dispersant due to the consequent high viscosity, or even solid, oil products which can be obtained. However, at lower DP's, oil soluble adducts possessing low viscosity and desirable sludge and varnish inhibition characteristics are obtained. Accordingly, regardless of the identity of the lactone adduct, the degree of polymerization (DP) should be between about 0.2 and about 100, more preferably between about 0.2 and about 50, and most preferably between 0.5 and about 20. For optimal dispersant performance sequences of from about 1 to about 5 lactone units in a row are preferred. The degree of polymerization can be controlled by controlling the reaction conditions, including the mole ratio of lactone to amine compound, amount of catalyst employed, and the like.

Useful amine compounds for reaction with the lactone material include polyamines of about 2 to 60, e.g. 3 to 20, most preferably 3 to 10, total carbon atoms in the molecule. These amines may be hydrocarbyl amines or may be hydrocarbyl amines including other noninterfering groups, e.g., alkoxy groups, amide groups, nitrile groups, imidazoline groups, and the like. Preferred amines are aliphatic saturated amines, including those of the general formula:

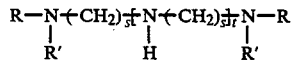

wherein R and R' are independently selected from the group consisting of hydrogen, $C_1$ to $C_{25}$ straight or branched chain alkyl radicals, $C_1$ to $C_{12}$ alkoxy $C_2$ to $C_6$ alkylene radicals, and $C_1$ to $C_{12}$ alkylamino $C_2$ to $C_6$ akylene radicals, each s is the same or a different number of from 2 to 6; preferably 2 to 4; and t is a number of from 0 to 10, preferable 2 to 7. If t=0, then at least one of R or R$^-$ must be H such that there are at least two of either primary or secondary amino groups.

Non-limiting examples of suitable amine compounds include: 1,2-diaminoethane: 1,3-diaminopropane: 1,4-diaminobutane; 1,6-diaminohexane; polyethylene amines such as diethylene triamine; triethylene tetramine; tetraethylene pentamine; polypropylene amines such as 1,2-propylene diamine; di-(1,2propylene) triamine; di-(1,3-propylene) triamine; N,N-dimethyl-1-1,3-diamino-propane; N,N-di-(2-aminoethyl) ethylene diamine; N-dodecyl-1-1,3-propane diamine; di-, and tritallow amine; amino morpholines such as N-(3-aminopropyl morpholine; etc.

Other useful amine compounds include: alicylic diamines such as 1,4-di(aminomethyl) cyclohexane, and heterocyclic nitrogen compounds such as imidazolines, morpholines, and N-aminolakyl piperazines of the general formula:

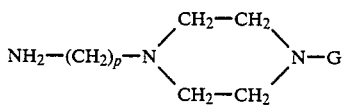

wherein G is independently selected from the group consisting hydrogen and omega-(nontertiary)aminoalkylene radicals of from 1 to 3 carbon atoms, and p is a number of from 1 to 4. Nonlimiting examples of such amines include 2-pentadecyl imidazoline, N-(2-aminoethyl) piperazine, etc.

Commercial mixtures of amine compounds advantageously may be used. For example, one process for preparing alkylene amines involves the reaction of an alkylene dihalide (such as ethylene dichloride or propylene dichloride) with ammonia, which results in a complex mixture of alkylene amines wherein pairs of nitrogens are joined by alkylene groups, forming such compounds as diethylene triamine, triethylenetetramine, tetraethylene pentamine and isomeric piperazines. A low cost mixture of poly(ethyleneamines) compounds averaging about 5 to 7 nitrogen atoms per molecule are available commercially under trade names as "Polyamine H", "Polyamine 400", "Dow Polyamine E-100", etc.

Useful amines also include polyoxalkylene polyamines such as those of the formulas:

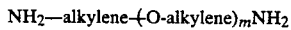

where m has a value of about 3 to 70 and preferably 10 to 35: and

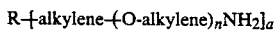

where n has a value of about 1 to 40 with the provision that the sum of all the n's is from about 3 to about 70 and preferably from about 6 to about 35. R is a substituted saturated hydrocarbon radical of up to 10 carbon atoms, wherein the number of substituents on the R group is represented by the value of "a", which is a number from 3 to 6. The alkylene groups in either formula III or IV may be straight or branched chain containing about 2 to 7, and preferably about 2 to 4 carbon atoms.

The above polyoxyalkylene polyamines, preferably polyoxyalkylene diamines and polyoxyalkylene triamines, may have average molecular weights ranging from about 200 to about 4,000 and preferably from about 400 to about 2,000. The preferred polyoxyalkylene polyamines include the polyoxyethylene and polyoxypropylene diamines and the polyoxypropylene triamines having average molecular weight ranging from about 200 to 2,000. The polyoxyalkylene polyamines are commercially available and my be obtained, for example, from the Jefferson Chemical Company, Inc. under the trade name "Jeffamines D-230, D-400, D-1000, D-2000, T-403", etc.

The polyamine is readily reacted with the lactone, with or without a catalyst, simply by heating a mixture of the lactone and polyamine in a reaction vessel in the absence of a solvent at a temperature of about 30° C. to about 200° C., more preferably to a temperature of about 75° C. to about 180° C., and most preferably at about 90° C. to about 160° C., for a sufficient period of time to effect reaction. Optionally, a solvent for the lactone, polyamine and/or adduct can be employed to control viscosity and/or reaction rates.

In one preferred embodiment of the invention, the $C_5$–$C_9$ lactone such as E-caprolactone is reacted with a polyamine such as tetraethylene pentamine in a 2:1 molar ratio in accordance with the Equation above. However, in accordance with the reaction scheme illustrated in Equation 3 above, it will be appreciated that the mole ratio of lactone to polyamine can be varied widely as a means for controlling the length of the sequence of lactone units in the adduct. In this latter regard, the mole ratio of lactone to polyamine may vary from about 10:1 to about 0.1:1, more preferably from about 4:1 to about 0.2:1, and most preferably from about 2:1 to about 0.4:1.

It also will be appreciated that the half ester may be formed, and that in most cases, the reaction product will comprise a mixture of the half ester and diester.

Catalysts useful in the promotion of the above identified lactone-polyamine reactions are selected from the group consisting of stannous octanoate, stannous hexanoate, stannous oxalate, tetrabutyl titanate, a variety of metal organic based catalyst acid catalysts and amine catalysts, as described on page 266, and forward in a book chapter authorized by R. D. Lundberg and E. F. Cox entitled, "Kinetics and Mechanisms of Polymerization: Ring Opening Polymerization", edited by Frisch and Reegen, published by Marcel Dekker in 1969, wherein stannous octanoate is an especially preferred catalyst. The catalyst is added to the reaction mixture at a concentration level of about 50 to about 10,000 parts per weight of catalyst per one million parts of the total reaction mixture.

REACTION OF THE LACTONE WITH A POLYOL

In another aspect of the invention, the lactone adduct dispersant precursors are prepared by reacting the above discussed $C_5$–$C_9$ lactones with a polyol instead of with a polyamine.

Suitable polyol compounds which can be used in this esterification reaction include aliphatic polyhydric alcohols containing up to about 100 carbon atoms and about 2 to about 10 hydroxyl groups. These alcohols can be quite diverse in structure and chemical composition, for example, they can be substituted or unsubstituted, hindered or unhindered, branched chain or straight chain, etc. as desired. Typical alcohols are alkylene glycols such as ethylene glycol, propylene glycol, trimethylene glycol, butylene glycol, and polyglycol such as diethylene glycol, triethylene glycol, tetraethylene glycol, dipropylene glycol, tripropylene glycol, dibutylene glycol, tributylene glycol, and other alkylene glycols and polyalkylene glycols in which the alkylene radical contains from two to about eight carbon atoms. Other useful polyhydric alcohols include glycerol, monomethyl ether of glycerol, penthaerythritol, dipentaerythritol, tripentaerythritol, 9,10-dihydroxystearic acid, the ethyl ester of 9,10-dihydroxystearic acid, 3-chloro-1, 2-propanediol, 1,2 butanediol, 1,4-butanediol, 2,3-hexanediol, 2,3-hexanediol, pinacol, tetrahydroxy pentane, erythritol, arabitol, sorbitol, mannitol, 1,2-cyclohexanediol, 1,4-cyclohexanediol, 1,4-(2-hydroxyethyl)-cyclohexane, 1,4-dihydroxy-2-nitrobutane, 1,4-di-(2-hydroxyethyl)-benzene, the carbohydrates such as glucose, rhamnose, mannose, glyceraldehyde, and galactose, and the like, amino alcohols such as di-(2-hydroxyethyl)amine, tri-(3-hydroxypropyl)amine, N,N'-di-(hydroxyethyl)ethylenediamine, copolymer of allyl alcohol and styrene, N,N-di-(2- hydroxylethyl) glycine and esters thereof with lower mono-and polyhydric aliphatic alcohols etc.

Included within the group of aliphatic alcohols are those alkane polyols which contain ether groups such as polyethylene oxide repeating units, as well as those polyhydric alcohols containing at least three hydroxyl groups, at least one of which has been esterified with a mono-carboxylic acid having from eight to about 30 carbon atoms such as octanoic acid, oleic acid, stearic acid, linoleic acid, dodecanoic acid, or tall oil acid, Examples of such partially esterified polyhydric alcohols are the mono-oleate of sorbitol, the mono-oleate of glycerol, the monostearate of glycerol, the di-stearate of sorbitol, and the di-dodecanoate of erythritol.

A preferred class of ester intermediates are those prepared from aliphatic alcohols containing up to 20 carbon atoms, and especially those containing three to 15 carbon atoms. This class of alcohols includes glycerol, erythritol, pentaerythritol, dipentaerythritol, tripentaerythritol, gluconic acid, glyceraldehyde, glucose, arabinose, 1,7-heptanediol, 2,4-heptanediol, 1,2,3-hexanetriol, 1,2,4-hexanetriol, 1,2,5-hexanetriol, 2,3,4-hexanetriol, 1,2,3-butanetriol, 1,2,4-butanetriol, quinic acid, 2,2,6,6-tetrakis(hydroxymethyl)-cyclohexanol, 1,10-decanediol, digitalose, and the like. The esters prepared from aliphatic alcohols containing at least three hydroxyl groups and up to fifteen carbon atoms are particularly preferred.

An especially preferred class of polyhydric alcohols for preparing the lactone adducts used as starting materials in the present invention are the polyhydric alkanols containing three to 15, especially three to six carbon atoms and having at least three hydroxyl groups. Such alcohols are exemplified in the above specifically identified alcohols and are represented by glycerol, erythritol, pentaerythritol, mannitol, sorbitol, 1,2,4-hexanetriol, and tetrahydroxy pentane and the like.

The polyol is readily reacted with $C_5$–$C_9$ lactone e.g., E-caprolactone, by heating a mixture of the polyol and lactone in a reaction vessel in the absence of a solvent at a temperature of about 50° C. to about 200° C., more preferably to a temperature of about 75° C. to about 180° C., and most preferable at about 90° C. to about 160° C., for a sufficient period of time to effect reaction. Optionally, a solvent for the lactone, polyol and/or the resulting adduct may be employed to control viscosity and/or the reaction rates.

In one preferred embodiment of the invention, the $C_5$–$C_9$ lactone, e.g., E-caprolactone is reacted with a polyol, e.g., pentaerythritol in accordance with the reaction scheme illustrated in Equation 5 wherein a 1:1 mole ratio of caprolactone to pentaerythritol is shown. In practice, the ratio of lactone to polyol may vary considerable as a means of controlling the length of the sequence of the lactone units in the adduct. For example, the mole ratio of lactone to polyol may vary from about 10:1 to about 0.1:1, more preferably from about 5:1 to about 0.2:1, and most preferably from about 2:1, to about 0.4:1. As is the case with the lactone/polyamine adducts, it is preferable to maintain the average degree of polymerization of the lactone monomer below about 100, with a degree of polymerization on the order of from about 0.2 to about 50 being preferred, and from about 0.2 to about 20 being more preferred. For optimum dispersant performance, sequences of from about 1 to about 5 lactone units in a row are preferred.

Catalysts useful in the promotion of the lactone-polyol reactions are the same as those which are useful in connection with the lactone-polyamine reactions discussed above. The catalyst may be added to the reaction mixture at a concentration level of from about 50 to about 10,000 parts of catalyst by weight per one million parts by weight of the total reaction mixture.

REACTION OF THE LACTONE WITH AN AMINO ALCOHOL

In a manner analogous to that described for the lactone-polyamine reaction and for the lactone-polyol reaction, the $C_5$–$C_9$ lactone can be reacted with an amino alcohol to form an adduct or intermediate which can be further reacted with an acylating agent to form the dispersants of this invention.

Suitable amino alcohol compounds which can be reacted with the lactone include those containing up to about 50 total carbon atoms and preferably up to about 10 total carbon atoms, from 1 to about 5 nitrogen atoms, preferably from 1 to 3 nitrogen atoms, and from 1 to about 15 hydroxyl groups, preferably from about 1 to 5 hydroxyl groups. Preferred amino alcohols include the 2,2-disubstituted-2-amino-1-alkanols having from two to three hydroxy groups and containing a total of 4 to 8 carbon atoms. These amino alcohols can be represented by the formula:

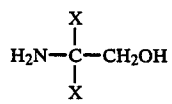

wherein X is an alkyl or hydroxyalkyl group with the alkyl groups having from 1 to 3 carbon atoms wherein at least one, and preferably both, of the X substituents is a hydroxyalkyl group of the structure —$(CH_2)_n$OH, n being 1 to 3. Examples of such amino alcohols include: 2-amino-2-methyl-1,3 propanediol; 2-amino-2-ethyl-1,3-propanediol; and 2-amino-2-(hydroxymethyl)1,3-propanediol; the latter also being known as THAM or tris (hydroxymethyl) amino methane. THAM is particularly preferred because of its effectiveness, availability and low cost.

The amino alcohol is readily reacted with the $C_5$–$C_9$ lactone by heating a mixture of the lactone and amino alcohol in a reaction vessel in the absence of a solvent at a temperature of about 50° C. to about 200° C., more preferably at temperature of about 75° C. to about 180° C., and most preferably at about 90° C. to about 160° C., for a sufficient period of time to effect reaction. Optionally, a solvent for the lactone, amino alcohol and/or the reaction product may be used to control viscosity and/or the reaction rates.

In one preferred embodiment of the invention, the $C_5$–$C_9$ lactone, e.g., E-caprolactone is reacted with an amino alcohol, e.g., THAM in accordance with the reaction scheme illustrated in Equation 7. As shown in Equation 7, one mole of E-caprolactone is reacted with one mole of THAM to form a polyhydroxy terminated amide which, upon further heating, rearranges to form a hydroxy-oxazoline.

It will be appreciated that the mole ratio of lactone to amino alcohol may be varied considerably and further that the reaction product, in most cases, will comprise a mixture of adducts. In this latter regard, it is contemplated that the mole ratio of lactone to amino alcohol may vary from about 10:1 to about 0.1:1, more preferably from about 5:1 to about 0.5:1, and most preferably from about 2:1 to about 0.6:1. It also contemplated that the average degree of polymerization of the lactone in the lactone/amino alcohol adduct preferably will be less than about 100. Preferably, the degree of polymerization is from about 0.2 to about 50, and more preferably from about 0.2 to about 20. For optimum dispersant performance, sequences of from about 1 to about 5 lactone units in a row are preferred.

Catalysts useful in the promotion of the lactone-amino alcohol reactions are the same as those which are useful in connection with the lactone-polyamine and lactone-polyol reactions, and corresponding amounts of catalyst may be employed.

THE ACYLATING AGENTS

The acylating agents which may be reacted with the lactone-polyamine, lactone-polyol and/or lactone-amino alcohol adducts to form the dispersant additives of the invention are saturated and unsaturated, straight chain or branched chain, natural or synthetic, aliphatic hydrocarbon monocarboxylic or dicarboxylic acylating agents, e.g., acid, anhydride or ester materials, which have from about 1 to about 165 total carbon atoms and from about 1 to about 85 carbon atoms in the straight or branched chain to insure hydrocarbon solubility of the acylated products.

In one preferred aspect, the acylating agent comprises an acid of the formula

RCOOH          VI where R is $C_1$–$C_{164}$ saturated or unsaturated, straight or branched aliphatic hydrocarbyl. Included are alkanoic, alkenoic and alkadienoic acids. Carboxylic acids wherein the hydrocarbyl portion of the molecule is of a straight chain configuration are preferred since, generally, less severe reaction conditions are required for acylation with such acid. Representative carboxylic acids include dodecanoic, dodecenoic, tridecanoic, tridecenoic, tetradecanoic, tetradecenoic, hexadecanoic, hexadecenoic, octadecanoic, octadecenoic, octadecadienoic, eicosandoic, uneicosanoic and deoicosanoic acids. Mixed acids can be employed, the mixture being preferred because of generally lower cost and better properties of fluidity and greater solubility. Acid mixtures such as those obtained by hydrolysis of natural fats and oils are useful. Included are those derived from coconut oil, corn oil, cottonseed oil, tallow and soybean oil. The acids prepared from tallow are ordinarily mixtures of tetradecanoic, tetradecenoic, hexadecanoic, hexadecenoic, octadecanoic, octadecenoic, octadecadienoic and eicosandoic acids; those prepared from soybean oil are mixtures containing hexadecanoic, octadecanoic, octadecadienoic and eicosanoic acids; those prepared from cotton seed oil are mixtures ordinarily containing tetradecanoic, hexadecanoic, octadecanoic, octadecadienoic and eicosanoic acids; and those prepared from cocanut oil contain decanoic, dodecanoic, tetradecanoic, hexadecanoic, octadecanoic, octadecenoic and octadecatrienoic acids with a very small amount of octanoic acid. A particularly useful and preferred acid mixture is tall oil fatty acid obtained from tall oil. Tall oil is a mixture of rosin and fatty acids released by acidulation of the black liquor soap skimmed off the black liquor from the sulfite process in the manufacture of Kraft paper. Crude tall oil is commonly fractionally distilled to provide various cuts wherein the ratio of fatty acids to rosin acids varies from 1:99 to 99:1. In the context of this description tall oil fatty acid is intended to include tall oil compositions having a fatty acid content of at least about 50% by weight, the balance being mainly rosin acids in admixture with minor amount of unsaponifiable materials of unknown chemical composition. The fatty acids in tall oil fatty acids consist mainly of oleic, linoleic, conjugated linoleic, palmitic, stearic, palmitoleic, arachidic and behenic acids. Tall oil fatty acids which are commercially available include those with the following compositions: palmitic (0.1–5.3%), palmitoleic (0.1–2.1%); stearic (2.1–2.6%); oleic (39.3–49.5%); linoleic (38.1–41.4%); eicosanoic (1.2–1.9%); eicosadienoic (0.5–3.2%); eicosatrienoic (0.4–2.9%); and behenic (0.4–0.9%) acids, with the balance being rosin acids, unidentified acids and unaponifiable materials.

In another preferred aspect, the acylating agent may comprise the dimer of a $C_{12}$–$C_{18}$ fatty acid. Specific fatty acid dimers which can be employed include the dimers of, for example, stearic acid, isostearic acid, linoleic acid, linolenic acid, oleic acid, 9, 11-octadecadienoic acid and eleostearic acid. Effective dimer acids can be prepared from naturally occurring materials, such as linseed fatty acids, soya bean fatty acids and other natural unsaturated fatty acids. A preparation of dimer acids is disclosed in U.S. Pat. No. 2,632,659. Suitable dimer acids are available commercially, for example, under the name Empol 1022 (a dimer of linoleic acid) and Empol 1010 (a dimer of acid). Both Empol 1022 and Empol 1010 are well known as rust inhibitors for motor fuel compositions.

Other suitable acylating agents include dicarboxylic acid materials, e.g., acid anhydride, or ester materials, which are substituted with a $C_{12}$–$C_{18}$ hydrocarbyl group, generally an alkenyl group, and which contain from about 0.7 to about 2.0, preferably 1.00 to 1.5 moles per mole of hydrocarbyl of an alpha or beta unsaturated $C_4$–$C_{10}$ dicarboxylic acid or anhydride or ester thereof, such as fumaric acid, itaconic acid, maleic acid, maleic anhydride, chloromaleic acid, dimethyl fumarate, chloromaleic anhydride, etc.

Preferred hydrocarbyl subtituents are alkyl, alkenyl and alkynyl groups containing from about twelve to about eighteen carbon atoms. Hydrocarbyl substituents of a straight chain configuration are preferred since they generally permit the use of less sever acylation conditions. Octadecenyl succinic anhydride is an example of a suitable hydrocarbyl substituted dicarboxylic acid material for use as the acylating agent in accordance with the present invention.

REACTION OF THE ACYLATING AGENT WITH THE LACTONE ADDUCT

In order to form the lactone based dispersants of the present invention, the acylating agent must be reacted with a lactone-polyamine adduct, a lactone-polyol adduct, a lactone-amino alcohol adduct or a mixture thereof.

All of the above lactone adducts are readily reacted with the acylating agent, e.g., isostearic acid, by heating a mixture of the lactone adduct and the acylating agent, with or without an oil diluent, to about 100° to 250° C., preferably 160° to 210° C., generally for 1 to 10, e.g., 2 to 6 hours, until the desired amount of water is removed. Reaction ratios can vary considerable, depending upon the reactants, amount of excess lactone adduct, type of bonds formed, etc. generally from 0.1 to 4.0 preferably 0.5 to 3.0 e.g., 0.5 to 1.0 moles of lactone adduct, e.g., E-caprolactone/pentaerythritol, are used per mole of the acylating agent moiety content. Variations beyond these ratios can be practiced, but normally such variations would not be desirable.

The reaction between the lactone-polyamine adduct and the acylating agent acid material may be exemplified by the following reaction scheme which which represents the esterification of stearic acid with an E-caprolactone/tetraethylene pentamine adduct:

Eq. 4

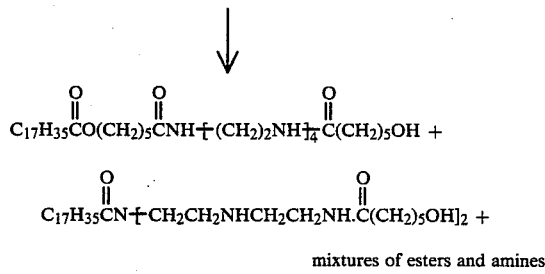

mixtures of esters and amines

In an alternative embodiment, the reaction between the lactone-polyol adduct and the acylating agent may be exemplified by the following reaction scheme which represents the esterification of the dimer acid of isostearic acid with an E-caprolactone/pentaerythritol adduct:

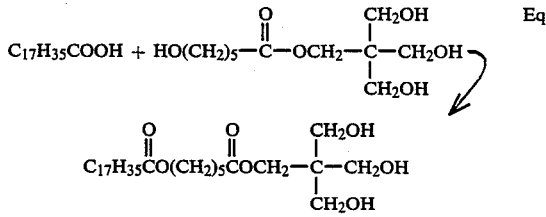

Eq. 6

In still another alternative a lactone/amino alcohol adduct is reacted with the carboxylic acylating agent to form a oxazoline type dispersant.

The preparation of the oxazoline type dispersants of this invention can be illustrated by the reactions between isostearic acid and E-caprolactone/THAM adducts as follows:

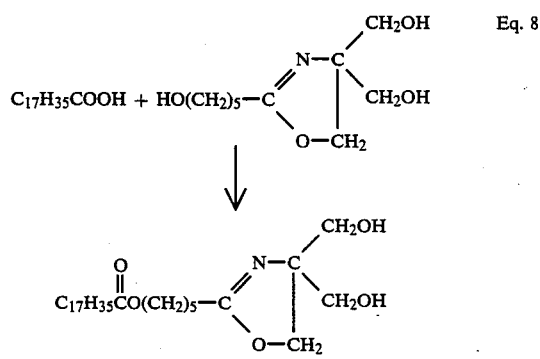

Eq. 8

Further aspects of the present invention reside in the formation of metal complexes and other post-treatment derivatives, e.g., borated derivatives, of the novel additives prepared in accordance with this invention. Suitable metal complexes may be formed in accordance with known techniques of employing a reactive metal ion species during or after the formation of the present $C_5$–$C_9$ lactone derived dispersant materials. Complex-forming metal reactants include the nitrates, thiocyanates, halides, carboxylates, phosphates, thio-phosphates, sulfates, and borates of transition metals such as iron, cobalt, nickel, copper, chromium, manganese, molybdenum, tungsten, ruthenium, palladium, platinum, cadmium, lead, silver, mercury, antimony and the like. Prior art disclosures of these complexing reactions may be found in U.S. Pat. Nos. 3,306,908 and Re. 26,433.

Post-treatment compositions include those formed by reacting the novel additives of the present invention with one or more post-treating reagents, usually selected from the group consisting of boron oxide, boron oxide hydrate, boron halides, boron acids, sulfur, sulfur chlorides, phosphorous sulfides and oxides, carboxylic acid or anhydride acylating agents, epoxides and episulfides and acrylonitriles. The reaction of such post-treating agents with the novel additives of this invention is carried out using procedures known in the art. For example, boration may be accomplished in accordance with the teachings of U.S. Pat. No. 3,254,025 by treating the $C_5$–$C_9$ lactone derived additive compound with a boron oxide, halide, ester or acid. Treatment may be carried out by adding about 1-3 wt. % of the boron compound, preferably boric acid, and heating and stirring the reaction mixture at about 135° C. to 165° C. for 1 to 5 hours followed by nitrogen stripping and filtration, if desired. Mineral oil or inert organic solvents facilitate the process.

THE COMPOSITIONS

The lactone derived additives of the present invention have been found to possess very good dispersant properties as measured herein in a wide variety of environments.

Accordingly, the lactone derived adducts are used by incorporation and dissolution into an oleaginous material such as fuels and lubricating oils.

When the dispersants of this invention are used in normally liquid petroleum fuels such as middle distillates boiling from about 150° to 800° F., including kerosene, diesel fuels, home heating fuel oil, jet fuels, etc., a concentration of the additive in the fuel in the range of typically from about 0.001 to 0.5, and preferably 0.001 to about 0.1 weight percent, based on the total weight of the composition, will usually be employed.

The lactone derived dispersant find their primary utility in lubricating oil compositions which employ a base oil in which the additives are dissolved or dispersed.

Such base oils may be natural or synthetic although the natural base oils will derive a greater benefit.

Thus, base oils suitable for use in preparing lubricating compositions of the present invention include those conventionally employed as crankcase lubricating oils for spark-ignited and compression-ignited internal combustion engines, such as automobile and truck engines, marine and railroad diesel engines, and the like. Advantageous results are also achieved by employing the dispersant additives of the present invention in base oils conventionally employed in and/or adapted for use as power transmitting fluids such as automatic transmission fluids, tractor fluids, universal tractor fluids and hydraulic fluids, heavy duty hydraulic fluids, power steering fluids and the like. Gear lubricants, industrial oils, pump oils and other lubricating oil compositions can also benefit from the incorporation therein of the additives of the present invention.

Thus, the additives of the present invention may be suitably incorporated into synthetic base oils such as alkyl esters of dicarboxylic acids, polyglycols and alcohols, polyalphaolefins, alkyl benzenes, organic esters of phosphoric acids, polysilicone oils, etc.

Natural base oils include mineral lubricating oils which may vary widely as to their crude source, e.g., whether paraffinic, naphthenic, mixed, paraffinic-naphthenic, and the like; as well as to their formation, e.g., distillation range, straight run or cracked, hydrofined, solvent extracted and the like.

More specifically, the natural lubricating oil base stocks which can be used in the compositions of this invention may be straight mineral lubricating oil or distillates derived from paraffinic, naphthenic, asphaltic, or mixed base crudes, or, if desired, various blends oils may be employed as well as residuals, particularly those from which asphaltic constituents have been removed. The oils may be refined by conventional methods using acid, alkali, and/or clay or other agents such as aluminum chloride, or they may be extracted oils produced, for example, by solvent extraction with solvents of the type of phenol, sulfur dioxide, furfural, dichlorodiethyl ether, nitrobenzene, crotonaldehyde, etc.

The lubricating oil base stock conveniently has a viscosity of typically about 2.5 to about 12, and preferably about 2.5 to about 9 cs. at 100° C.

Thus, the lactone derived additives of the present invention can be employed in a lubricating oil the oil by dispersing, or dissolving the same in the oil at the desired level of concentration typically with the aid of a suitable solvent such as toluene, or tetrahydrofuran. Such blending can occur at room temperature or elevated temperatures. Alternatively, the dispersant additives may be blended with a suitable oil-soluble solvent and base oil to form a concentrate, and then blending the concentrate with lubricating oil base stock to obtain the final formulation. Concentrates will typically contain from about 20 to about 60 wt. %, by weight dispersant additive, and typically from about 80 to about 20%, preferably from about 60 to about 20% by weight base oil, based on the concentrate weight.

The lubricating oil base stock for the dispersant additives of the present invention typically is adapted to perform a selected function by the incorporation of additives therein to form lubricating oil compositions (i.e, formulations).

Representative additives typically present in such formulations include viscosity modifiers, corrosion inhibitors, oxidation inhibitors, friction modifiers, other dispersants, anti-foaming agents, anti-wear agents, pour point depressants, detergents, rust inhibitors and the like.

Viscosity modifiers impart high and low temperature operability, to the lubricating oil and permit it to remain shear stable at elevated temperatures and also exhibit acceptable viscosity or fluidity at low temperatures.

Viscosity modifiers are generally high molecular weight hydrocarbon polymers including polyesters. The viscosity modifiers may also be derivatized to include other properties or functions, such as the addition of dispersancy properties. composition which comprises lubricating oil, typically in a major amount, and the dispersant additive, typically in a minor amount, which is effective to impart enhanced dispersancy, relative to the absence of the additive. Additional conventional additives selected to meet the particular requirements of a selected type of lubricating oil composition can be included as desired.

The dispersants of this invention are oil-soluble, dissolvable in oil with the aid of a suitable solvent, or are stably dispersible materials. Oil-soluble, dissolvable, or stably dispersible as that terminology is used herein does not necessarily indicate that the materials are soluble, dissolvable, miscible, or capable or being suspended in oil in all proportions. It does means, however, that the dispersant additives, for instance, are soluble or stably dispersible in oil to an extent sufficient to exert their intended effect in the environment in which the oil is employed. Moreover, the additional incorporation of other additives may also permit incorporation of higher levels of a particular dispersant, if desired.

Accordingly, while any effective amount of the dispersant additives can be incorporated into the lubricating oil composition, it is contemplated that such effective amount be sufficient to provide said lube oil composition with an amount of the additive of typically from about 0.10 to about 15 e.g., 0.1 to 10, and preferably from about 0.1 to about 7 wt. %, based on the weight of said composition.

The dispersant additives of the present invention can be incorporated into the lubricating oil in any convenient way. Thus, they can be added directly to These oil soluble viscosity modifying polymers will generally have number average molecular weights of from $10^3$ to $10^6$, preferably $10^4$ to $10^6$, e.g., 20,000 to 250,000, as determined by gel permeation chromatography or membrane osmometry.

Representative examples of suitable viscosity modifiers are any of the types known to the art including polyisobutylene, copolymers of ethylene and propylene, polymethacrylates, methacrylate copolymers, copolymers of an unsaturated dicarboxylic acid and vinyl compound, interpolymers of styrene and acrylic esters, and styrene/isoprene copolymers.

Corrosion inhibitors, also known as anti-corrosive agents, reduce the degradation of the metallic parts contacted by the lubricating oil composition. Illustrative of corrosion inhibitors are phosphosulfurized hydrocarbons and the products obtained by reaction of a phosphosulfurized hydrocarbon with an alkaline earth metal oxide or hydroxide, preferably in the presence of an alkylated phenol or of an alkylphenol thioester, and also preferably in the presence of carbon dioxide. Phosphosulfurized hydrocarbons are prepared by reacting a suitable hydrocarbon such as a terpene, a heavy petroleum fraction of a $C_2$ to $C_6$ olefin polymer such as polyisobutylene, with from 5 to 30 wt. % of a sulfide of phosphorus for ½ to 15 hours, at a temperature in the range of 150° to 600° F. Neutralization of the phosphosulfurized hydrocarbon may be effected in the manner taught in U.S. Pat. No. 1,969,324.

Oxidation inhibitors reduce the tendency of mineral oils to deteriorate in service which deterioration can be evidenced by the products of oxidation such as sludge and varnish-like deposits on the metal surfaces and by viscosity growth. Such oxidation inhibitors include alkaline earth metal salts of alkylphenolthioesters having preferably $C_5$ to $C_{12}$ alkyl side chains, e.g., calcium nonylphenol sulfide, barium t-octylphenyl sulfide, dioctylphenylamine, phenylalphanaphthylamine, phosphosulfurized or sulfurized hydrocarbons, etc.

Friction modifiers serve to impart the proper friction characteristics to lubricating oil compositions such as automatic transmission fluids.

Representative examples of suitable modifiers are found in U.S. Pat. No. 3,933,659 which discloses fatty acid esters and amides; U.S. Pat. No. 4,176,074 which describes molybdenum complexes of polyisobutyenyl succinic anhydride-amino alkanols; U.S. Pat. No. 4,105,571 which discloses glycerol esters of dimerized fatty acids; U.S. Pat. No. 3,779,928 which discloses alkane phosphonic acid salts; U.S. Pat. No. 3,778,375 which discloses reaction products of a phosphonate with an oleamide; U.S. Pat. No. 3,852,205 which discloses S-carboxyalkylene hydrocarbyl succinimide, S-carboxyalkylene hydrocarbyl succinamic acid and mixtures thereof; U.S. Pat. No. 3,879,306 which discloses N-(hydroxyalkyl)alkenyl-succinamic acids or succinimides; U.S. Pat. No. 3,932,290 which discloses reaction products of di-(lower alkyl) phosphites and epoxides; and U.S. Pat. No. 4,028,258 which discloses the alkylene oxide adduct of phosphosulfurized N-(hydroxyalkyl) alkenyl succinimides. The disclosures of the above references are herein incorporated by reference. The most preferred friction modifiers are succinate esters, or metal salts thereof, or hydrocarbyl substituted succinic acids or anhydrides and thiobis alkanols such as described in U.S. Pat. No. 4,344,853.

Dispersants maintain oil insolubles, resulting from oxidation during use, in suspension in the fluid thus preventing sludge flocculation and precipitation or deposition on metal parts. Suitable dispersants include high molecular weight alkyl succinates, the reaction product of oil-soluble polyisobutylene succinic anhydride with ethylene amines such as tetraethylene pentamine and borated salts thereof.

Pour point depressants lower the temperature at which the fluid will flow or can be poured. Such depressants are well known. Typically of those additives which usefully optimize the low temperature fluidity of the fluid are $C_8$–$C_{18}$ dialkylfumarate vinyl acetate copolymers, polymethacrylates, and way naphthalene. Foam control can be provided by an antifoamant of the polysiloxane type, e.g., silicone oil and polydimethyl siloxane.

Anti-wear agents, as their name implies, reduce wear of metal parts. Representatives of conventional anti-wear agents are zinc dialkyldithiophosphate, and zinc diaryldithiosphate.

Detergents and metal rust inhibitors include the metal salts of sulphonic acids, alkyl phenols, sulfurized alkyl phenols, alkyl salicylates, naphthenates and other oil soluble mono- and di-carboxylic acids. Highly basic (viz, overbased) metal salts, such as highly basic alkaline earth metal sulfonates (especially Ca and Mg salts) are frequently used as detergents. Representative examples of such materials, and their methods of preparation, are found in co-pending Ser. No. 754,001, filed July 11, 1985, the disclosure of which is hereby incorporated by reference.

Some of these numerous additives can provide a multiplicity of effects, e.g., a dispersant-oxidation inhibitor. This approach is well known and need not be further elaborated herein.

Compositions when containing these conventional additives are typically blended into the base oil in amounts which are effective to provide their normal attendant function. Representative effective amounts of such additives are illustrated as follows:

| Additive | Vol % | Wt % a.i. |
| --- | --- | --- |
| Viscosity Modifier | .01–4 | .01–4 |
| Corrosion Inhibitor | 0.01–1 | .01–1.5 |
| Oxidation inhibitor | 0.01–1 | .01–1.5 |
| Dispersant | 0.1–7 | 0.1–8 |
| Pour Point Depressant | 0.01–1 | .01–1.5 |
| Anti-Foaming Agents | 0.001–0.1 | .001–0.15 |
| Anti-Wear Agents | 0.001–1 | .001–1.5 |
| Friction Modifiers | 0.01–1 | .01–1.5 |
| Detergents/Rust Inhibitors | .01–2.5 | .01–3 |
| Mineral Oil Base | Balance | Balance |

When other additives are employed, it may be desirable, although not necessary, to prepare additive concentrates comprising concentrated solutions or dispersions of the dispersant (in concentrate amounts hereinabove described), together with one or more of said other additives (said concentrate when constituting an additive mixture being referred to herein as an additive-package) whereby several additives can be added simultaneously to the base oil to form the lubricating oil composition. Dissolution of the additive concentrate into the lubricating oil may be facilitated by solvents and by mixing accompanied with mild heating, but this is not essential. The concentrate or additive-package will typically be formulated to contain the dispersant additive and optional additional additives in proper amounts to provide the desired concentration in the final formulation when the additive-package is combined with a predetermined amount of base lubricant. Thus, the dispersant of the present invention can be added to small amounts of base oil or other compatible solvents along with other desirable additives to form additive-packages containing active ingredients in collective amounts of typically from about 2.5 to about 90%, and preferably from about 5 to about 75%, and most preferably from about 8 to about 50% by weight additives in the appropriate proportions with the remainder being base oil.

The final formulations may employ typically about 10 wt. % of the additive-package with the remainder being base oil.

All of said weight percents expressed herein are based on active ingredient (a.i.) content of the additive, and/or upon the total weight of any additive-package, or formulation which will be the sum of the a.i. weight of each additive plus the weight of total oil or diluent.

This invention will be further understood by reference to the following examples, wherein all parts are parts by weight and all molecular weights are number average molecular weights, unless otherwise noted and which include preferred embodiments of the invention.

Example 1

Preparation of Isostearic Acid/E-Caprolactone-TEPA Dispersant

About 37.8 g (0.2 mole) of tetraethylene pentamine (TEPA) were mixed with 22.8 g (0.2 mole) of E-caprolactone (CL) in a 500 ml flask. The mixture stirred at room temperature for two hours and then heated slowly to 110° C. The mixture was kept at that temperature for one hour while stirring under a nitrogen blanket.

Thereafter, 176.4 g of isostearic acid (ISA) were added over a period of 40 minutes while maintaining the temperature at 110° C. The reaction temperature was raised to 160° C. over a period of three hours. A vacuum was then applied and the reaction mixture was heated to 190° C. for two hours.

EXAMPLE 2

Simultaneous Reaction of TEPA E-Caprolactone and Isostearic Acid.

About 176.4 g (0.62 moles) of isostearic acid 22.8 g (0.2 mole) of E-caprolactone and 37.8 g (0.2 moles) of TEPA were added to a reactions flask. The reaction mixture was blanketed with nitrogen and heated to 160° C. for two hours. A vacuum was applied and the reaction mass was heated to 190° C. for two hours.

EXAMPLE 3

Preparation of Isostearic Acid—TEPA Reaction Product

About 88.2 g (0.31 moles) of isostearic acid were added to a reaction flask and 37.8 g (0.2 moles) TEPA were added over a 30 minute period. Then another 88.2 g of isostearic acid were added over a 30 minute period. The reaction temperature was raised to 160° C. over a three hour period. The nitrogen blanket was removed, a vacuum was applied, and the temperature was raised to 190° C. for two hours.

Samples of the various reaction products of Example 1, 2 and 3, along with samples of several commercially employed dispersants were then subjected to a standard sludge inhibition bench test (SIB) and a standard varnish inhibition bench test (VIB).

The SIB and VIB tests forecast the performance of a lubricant in a gasoline engine. These tests are described below. The SIB test employs a used crankcase mineral lubricating oil composition having an original viscosity of about 325 SUS at 37.8° C. that have been used in a taxicab that was driven generally for short trips only, thereby causing a buildup of a high concentration of sludge precursors. The oil used contains only a refined base mineral oil, a viscosity index improver, a pour point depressant and zinc dialkyl-dithiophosphate antiwear additives. The oil contains no sludge dispersants. Such oil is acquired by draining and refilling the taxicab crankcases at about 1000-2000 mile intervals.

The SIB test is conducted in the following manner: The used crankcase oil is freed of sludge by centrifuging for one half hour at about 39.000 gravities (gs). The resulting clear bright red oil is then decanted from the insoluble particles. However, the supernatant oil still contains oil-soluble sludge precursors which, under the conditions employed by this test, tend to form additional oil-insoluble deposits of sludge. The sludge inhibiting properties of the additives being tested are determined by adding to portions of the used oil 0.5 wt. % on an active basis, of the particular additive being tested. Ten grams of each sample being tested is placed in a stainless steel centrifuge tube and is heated at 140° C. for 16 hours in the presence of air. Following the heating, the tube containing the oil being tested is cooled and then centrifuged for 30 minutes at about 39,000 gs. Any deposits of new sludge that form in this step are separated from the decanting supernatant oil and then carefully washed with 15 ml. of pentane to remove all remaining oils from the sludge. The weight, in milligrams, of the new solid sludge that forms in the test is determined by drying the residue and weighing it. The results are reported as milligrams of sludge per ten grams of oil thus measuring differences as small as one part per ten thousand. The less new sludge formed, the more effective is the additive as a dispersant. In other words, if the additive is effective, it will hold at least a portion of the new sludge that forms on heating and oxidation, stably suspended in the oil so that it does not precipitate during the centrifuging period.

In the VIB test, a test sample consisting of ten grams of lubricating oil containing 0.5 wt. %, on an active basis, of the additive being evaluated is used. The test oil is a commercial lubricating oil obtained from a taxi after about 2000 miles of driving with said lubricating oil. Each sample is heat soaked overnight at about 140° C. and thereafter centrifuged to remove the sludge. The supernatant fluid of each sample is subjected to heat cycling from about 150° C. to room temperature over a period of 3.5 hours at a frequency of about two cycles per minute. During the heating phase, a gas containing a mixture of 0.7 volume percent $SO_2$, 1.4 volume percent NO and the balance air is bubbled through the test samples and during the cooling phase, water vapor was bubbled through the test samples. At the end of the test period, which testing cycle can be repeated as necessary to determine the inhibiting effect of any additive, the wall surfaces of the test flasks in which the samples were contained are visually evaluated as to the varnish inhibition. The amount of varnish deposited on the walls is rated at values of from one to eleven with the higher number being the greater amount of varnish. It has been found that this test forecasts the varnish results obtained as a consequence of carrying out the ASTM MS-VD engine tests which is described more fully hereinbelow.

Table I, which follows, summarizes the compositions tested and the test results:

TABLE I

| Example | Process | TEPA[1] (moles) | CL[2] (moles) | ISA[3] (moles) | Viscosity, 100° C., CS | SIB[4] | SIB[5] |
|---------|---------|-----------------|---------------|----------------|------------------------|--------|--------|
| 1 | Pre-reacted[6] TEPA-CL | 1 | 2 | 3.1 | 112.4 | 7.91 | 3 |
| 2 | Simultaneous[7] | 1 | 1 | 3.1 | 90.4 | 6.93 | 3¾ |
| 3 | Simultaneous[8] Addition | 1 | 0 | 3.1 | 58.6 | 1.35 | 4 |
| PIBSA 1[9] | | | | | | 3.26 | 7 |
| PIBSA 2[10] | | | | | | 2.23 | 5 |

TABLE I-continued

| Example | Process | TEPA[1] (moles) | CL[2] (moles) | ISA[3] (moles) | Viscosity, 100° C., CS | SIB[4] | SIB[5] |
|---|---|---|---|---|---|---|---|
| ISA TEPA[11] | | | | | 105.2 | .93 | 4¼ |

[1]tetraethylene pentamine
[2]caprolactone
[3]isostearic acid
[4]sludge inhibition bench test rating in milligrams sludge per 10 milligrams oil
[5]varnish inhibition bench test rating on basic of 1 to 11; the higher the rating, the greater the amount of varnish deposited
[6]TEPA reacted with CL to form adduct which is then reacted with ISA
[7]simultaneous reaction of TEPA, CL and ISA
[8]simultaneous reaction of TEPA and ISA
[9]polyisobutenyl succinic anhydridge dispersant; number average Mw of polyisobutylene moieties (PIB) = 940; ratio of succinic anhydride (SA) moieties to PIB moieties = 1.04
[10]polyisobutenyl succinic anhydridge dispersant; number average Mw of polyisobutylene moieties (PIB) = 1300; ratio of succinic anhydride (SA) moieties to PIB moieties = 1.31
[11]pilot plant version of Example 3.

The data in Table I indicate that the dispersants prepared by reacting isostearic acid with the caprolactone-TEPA adduct (Example 1) showed an improved VIB value when compared to the dispersants prepared by the simultaneous addition of TEPA, CL and ISA (Example 2) or the simultaneous addition of TEPA and ISA, without any addition of CL (Example 3). The data also indicate that the dispersant prepared in accordance with the invention exhibits substantially better VIB ratings than commercially employed dispersants based on polyisobutenyl succinic anhydride (PIBSA 1 and PIBSA 2) and (ISA TEPA), and that while there is an increase in viscosity with then CL is present in the dispersants, the overall viscosity of the pre-reacted TEPA-CL/ISA dispersant is comparable to that of the ISA TEPA dispersant. It will be noted that the SIB and VIB tests of the products shown in Table 1 were based on a 100% active ingredient material so that a relative comparison to the ISA TEPA dispersant could be made. It will be noted also that although the SIB values are somewhat higher for the dispersants which contain CL, all of the SIB values shown in Table 1 are well within commercially acceptable limits.

Other lactone adduct dispersants in accordance with the present invention are illustrated in Example 4–9, which follow.

EXAMPLE 4

Preparation of E-Caprolactone-THAM Adduct

About 121.0 g (1.0 mole) of 2-amino-2-(hydroxymethyl)-1,3-propanediol (THAM) was combined with 114.0 g (1.0 mole) of E-Caprolactone and 0.1 g stannous octanoate $Sn(OCT)_2$. As the reaction mixture was slowly heated to 150° C., a clear solution was obtained. Infrared analysis of the reaction product showed no unreacted caprolactone. Upon heating the product cyclized to a hydroxy-oxazoline, and a strong absorption band at 6.0 microns in the infrared spectrum was observed. The product analyzed for 50.94% C, 9.29% H and 5.79% N.

EXAMPLE 5

Preparation of Dimer Acid/E-Caprolactone-THAM Adduct Dispersant

About 141.2 g (0.25 moles) of a dimer of linoleic acid (Empol 1010 from Emery Chemical Company), and 117.5 g (0.5 moles) of the caprolactone-THAM adduct of Example 4 were charged into a reaction flask, along with 0.1 g of para-toluene sulfonic acid (p-TOSH). The reaction mixture was slowly heated to 180° C. while stirring under a nitrogen blanket. At the end of four hours at 180° C., an infrared analysis of the reaction mixture showed complete conversion to the desired ester oxazoline. The reaction mixture as then cooled and collected.

EXAMPLE 6

Preparation of Octadecenyl Succinic Anhydride/E-Caprolactone-THAM Adduct Dispersant About 87.5 g (0.25 moles) of octadecenyl succinic anhydride (OSA), 117.4 g (0.5 moles) of the CL-THAM adduct of Example 4 and 0.1 g of p-TOSH were added to a 500 ml. flask and slowly heated to 180° C. while under a nitrogen atmosphere. The reaction mixture was checked periodically by infrared analysis. At the end of the fourth hour at 180° C., while under nitrogen, the infrared analysis showed complete conversion to the desired ester oxazoline. The reaction mixture was then cooled and collected.

EXAMPLE 7

Preparation of Isostearic Acid/E-Caprolactone-THAM Adduct Dispersant

About 28.1 g (0.1 mole) of isostearic acid and 23.5 g (0.1 mol) of the CL-THAM adduct of Example 4 were added to a reaction flask and heated to 180° C. to distill off the water of reaction. The reaction mixture was heated at 180° C. for four hours with mild nitrogen sparging. An infrared analysis of the product showed the desired ester oxazoline. The residue was diluted in solvent 150 neutral mineral oil to make a 50% active ingredient solution and was collected.

EXAMPLE 8

Preparation of E-Caprolactone Pentaerythritol Adduct

About 163.2 g (1.2 moles) of pentaerythritol (PE) and 136.2 g (1.2 moles) of E-caprolactone were mixed with 0.1 g of $Sn(OCT)_2$ and heated slowly to 150° C. for one hour. An infrared analysis of the product showed complete reaction of the caprolactone and PE. The product was poured into a large excess of methanol and no unreacted PE precipitated out of the solution. The methanol was stripped off and the residue was collected. The product became a waxy solid upon standing at room temperature.

EXAMPLE 9

Preparation of Dimer Acid E-Caprolactone-PE Adduct Dispersant

About 141.2 g (0.25 moles) of Empol 1010 dimer acid from Emery Chemical Company, about 137.5 g (approximately 0.5 moles) of the caprolactone-PE adduct of Example 8, and about 0.1 g of p-TOSH were added to a 500 ml flask and slowly heated to 180° C. while stirring under a nitrogen atmosphere. At the end of four hours at 180° C., an infrared analysis of the reaction mixture showed complete conversion to the desired ester.

As will be evident to those skilled in the art, various modifications on this invention can be made or followed, in light of the foregoing disclosure and illustrative examples, tables and discussion, without departing from the spirit and scope of the disclosure or from the scope of the invention as set forth in the following claims.

What is claimed is:

1. A $C_5-C_9$ lactone adduct material useful as an oil additive formed by reacting an aliphatic hydrocarbyl saturated or unsaturated, natural or synthetic, straight chain or branched chain monocarboxylic or dicarboxylic acylating agent heaving from about 1 to about 165 total carbon atoms with the reaction product of a $C_5-C_9$ lactone with a member selected from the group consisting of (a) a polyamine having from about 2 to 60 total carbon atoms and from about 2 to about 12 nitrogen atoms, (b) an amino alcohol containing up to about 50 total carbon atoms, from 1 to about 5 nitrogen atoms and from 1 to about 15 hydroxyl groups, and (c) mixtures of (a) and (b), said aliphatic acylating agent having at least about twelve carbon atoms in said straight or branched chain to produce lactone adduct material that is hydrocarbon soluble.

2. The $C_5-C_9$ lactone adduct material of claim 1, wherein said acylating agent is a member selected from the group of long chain fatty acids or dimers thereof and hydrocarbyl substituted $C_4-C_{10}$ monounsaturated dicarboxylic acid materials, wherein said hydrocarbyl group contains from about twelve to about eighteen carbon atoms.

3. The $C_5-C_9$ lactone adduct material of claim 2, wherein said lactone is E-caprolactone.

4. The $C_5-C_9$ lactone adduct material of claim 3, wherein said acylating agent is selected from the group consisting of isostearic acid, stearic acid, linoleic acid, oleic acid, dimers of said acids and octadecenyl succinic anhydride.

5. The $C_5-C_9$ lactone adduct material of claim 1, wherein said $C_5-C_9$ lactone is reacted with a polyamine, and wherein said polyamine is an aliphatic saturated amine having the formula:

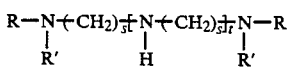

wherein R and R' independently are selected from the group consisting of hydrogen; $C_1$ to $C_{25}$ straight or branched chain alkyl radicals; $C_1$ to $C_{12}$ alkoxy $C_2$ to $C_6$ alkylene radicals; and $C_1$ to $C_{12}$ alkylamino $C_2$ to $C_6$ alkylene radicals; each s is the same or a different number of from 2 to 6, and t is a number of from 0 to 10, with the provision that when t=0, at least one of R or R' must be H such that there are at least two of either primary or secondary amino groups.

6. The $C_5-C_9$ lactone adduct material of claim 5, wherein said amine is selected from the group consisting of 1,2-diaminoethane; 1,3-diaminopropane; 1,4-diaminobutane; 1,6-diaminohexane; diethylene triamine; triethylene tetramine; tetraethylene pentamine; 1,2-propylene diamine; di-(1, 2-propylene)triamine; di-(1,3-propylene) triamine; N, N-dimethyl-1,3-diaminopropane; N, N-di-(2-aminoethyl) ethylene diamine; and N-dodecyl-1,3-propane diamine.

7. The $C_5-C_9$ lactone adduct material of claim 1, wherein said amine is selected from the group consisting of alicyclic diamines, imidazolines, morpholines and N-aminoalkyl piperazines of the general formula:

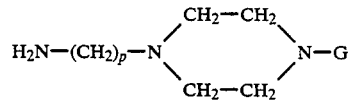

wherein G is independently selected from the group consisting of hydrogen and omega(nontertiary)-aminoalkylene radicals of from 1 to 3 carbon atoms, and p is a number of from 1 to 4.

8. The $C_5-C_9$ lactone adduct material of claim 1, wherein said polyamine is a mixture of poly (ethyleneamines) averaging about 5 to about 7 nitrogen atoms per molecule.

9. The $C_5-C_9$ lactone adduct material of claim 1, wherein said polyamine is a polyoxyalkylene polyamine having the formula:

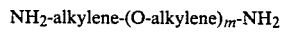

wherein m has a value of about 3 to 70: or

wherein n has a value of about 1 to 40 with the provision that the sum of all the n's is from about 3 to about 70, R is a substituted saturated hydrocarbon radical of up to 10 carbon atoms, wherein the number of subtituents on the R group is represented by the value of "a", which is a number from 3 to 6.

10. The $C_5-C_9$ lactone adduct material of claim 4, wherein said $C_5-C_9$ lactone is reacted with a polyamine, and wherein said polyamine is an aliphatic saturated amine having the formula:

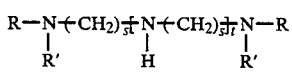

wherein R and R' independently are selected from the group consisting of hydrogen; $C_1$ to $C_{25}$ straight or branched chain alkyl radicals; $C_1$ to $C_{12}$ alkoxy $C_2$ to $C_6$ alkylene radicals; and $C_1$ to $C_{12}$ alkylamino $C_2$ to $C_6$ alkylene radicals; each s is the same or a different number of from 2 to 6, and t is a number of from 0 to 10, with the provision that when t=0, at least one of R or R' must be H such that there are at least two of either primary or secondary amino groups.

11. The $C_5-C_9$ lactone adduct material of claim 10, wherein said amine is selected from the group consisting of 1,2-diaminoethane; 1,3-diaminopropane; 1,4-diaminobutane; 1,6-diaminohexane; diethylene triamine; triethylene tetramine; tetraethylene pentamine; 1,2-propylene diamine; di-(1,2-propylene)triamine; di-(1,3-propylene) triamine; N, N-dimethyl-1,3-diaminopropane; N,N-di-(2-aminoethyl) ethylene diamine; and N-dodecyl-1,3-propane diamine.

12. The $C_5-C_9$ lactone adduct material of claim 4, wherein said polyamine is selected from the group consisting alicyclic diamines, imidazolines, morpholines and N-aminoalkyl piperazines of the general formula:

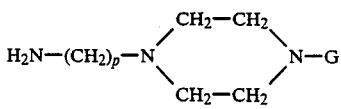

wherein G is independently selected from the group consisting of hydrogen and omega-(nontertiary)aminoalkylene radicals of from 1 to 3 carbon atoms, and p is a number of from 1 to 4.

13. The $C_5$-$C_9$ lactone adduct material of claim 4, wherein said polyamine is a mixture of poly (ethyleneamines) averaging about 5 to about 7 nitrogen atoms per molecule.

14. The $C_5$-$C_9$ lactone adduct material of claim 4, wherein said polyamine is a polyoxyalkylene polyamine having the formula:

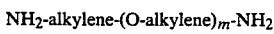

wherein m has a value of about 3 to 70: or

wherein n has a value of about 1 to 40 with the provisions that the sum of all the n's is from about 3 to about 60, R is a substituted saturated hydrocarbon radical of up to 10 carbon atoms, wherein the number of substituents on the R group is represented by the value of "a", which is a number from 3 to 6.

15. The $C_5$-$C_9$ lactone adduct material of claim 1, wherein said $C_5$-$C_9$ lactone is reacted with an amino alcohol.

16. The $C_5$-$C_9$ lactone adduct material of claim 15, wherein said amino alcohol is a 2,2-disubstituted-2-amino-1-alkanol of the formula

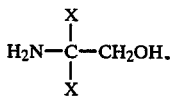

wherein X is alkyl or hydroxyalkyl group with the alkyl groups having from 1 to 3 carbon atoms, wherein at least one of the X substituents is a hydroxyalkyl group of the formula $(CH_2)_nOH$, and wherein n is 1 to 3.

17. The $C_5$-$C_9$ lactone adduct mateial of claim 16, wherein said amino alcohol is tris (hydroxymethyl) amino methane.

18. The $C_5$-$C_9$ lactone adduct material of claim 4, wherein said $C_5$-$C_9$ lactone is reacted with an amino alcohol.

19. The $C_5$-$C_9$ lactone adduct material of claim 18, wherein said amino alcohol is a 2,2-disubstituted-2-amino-1-alkanol of the formula:

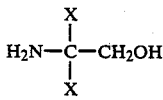

wherein X is alkyl or hydroxyalkyl group with the alkyl groups having from 1 to 3 carbon atoms, wherein at least one of the X substituents is a hydroxyalkyl group of the formula $(CH_2)_nOH$, and wherein n is 1 to 3.

20. The $C_5$-$C_9$ lactone adduct material of claim 19, wherein said amino alcohol is tris (hydroxymethyl) amino methane.

21. A process for preparing a $C_5$-$C_9$ lactone adduct material useful as an oil additive, which comprises the steps of:
(i) reacting a $C_5$-$C_9$ lactone with a member selected from the group consisting of (a) polyamines having from about 2 to about 60 total carbon atoms and from about 2 to about 12 nitrogen atoms, (b) amino alcohols containing up to about 50 total carbon atoms, from 1 to about 5 nitrogen atoms, and from 1 to about 15 hydroxyl groups, and (c) mixtures of (a) and (b) to form a lactone adduct intermediate product; and
(ii) reacting said intermediate product with an aliphatic hydrocarbyl saturated or unsaturated, natural or synthetic, straight chain or branched chain monocarboxylic or dicarboxylic acylating agent having from about twelve to about eighteen total carbon atoms and at least twelve carbon atoms in the hydrocarbyl group.

22. The process of claim 21, wherein said acylating agent is a member selected from the group of long chain fatty acids or dimers thereof and hydrocarbyl substituted $C_4$-$C_{10}$ monounsaturated dicarboxylic acid materials, wherein said hydrocarbyl group contains from about twelve to about eighteen carbon atoms.

23. The process of claim 22, wherein said $C_5$-$C_9$ lactone is reacted with a polyamine, and wherein said polyamine is an aliphatic saturated amine having the formula:

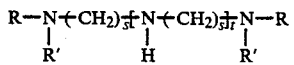

wherein R and R' independently are selected from the group consisting of hydrogen; $C_1$ to $C_{25}$ straight or branched chain alkyl radicals; $C_1$ to $C_{12}$ alkoxy $C_2$ to $C_6$ alkylene radicals; and $C_1$ to $C_{12}$ alkylamino $C_2$ to $C_6$ alkylene radicals; each s is the same or a different number of from 2 to 6, and t is a number of from 0 to 10, with the provision that when t=0, at least one of R or R' must be H such that there are at least two of either primary or secondary amino groups.

24. The process of claim 22, wherein said lactone is E-caprolactone.

25. The process of claim 24, wherein said acylating agent is selected from the group consisting of isostearic acid, stearic acid, linoleic acid, oleic acid, dimers of said acids and octadecenyl succinic anhydride.

26. The process of claim 24, wherein said $C_5$-$C_9$ lactone is reacted with a polyamine, and wherein said polyamine is an aliphatic saturated amine having the formula:

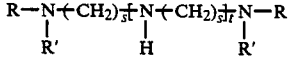

wherein R and R' independently are selected from the group consisting of hydrogen; $C_1$ to $C_{25}$ straight or branched chain alkyl radicals; $C_1$ to $C_{12}$ alkoxy $C_2$ to $C_6$ alkylene radicals; and $C_1$ to $C_{12}$ alkylamino $C_2$ to $C_6$ alkylene radicals; each s is the same or a different number of from 2 to 6, and t is a number of from 0 to 10, with the provision that when t=0, at least one of R or R' must be H such that there are at least two of either primary or secondary amino groups.

27. The process of claim 26, wherein said amine is selected from the group consisting of 1,2-diaminoethane; 1,3-diaminopropane; 1,4-diaminobutane; 1,6-diaminohexane; diethylene triamine; triethylene tetramine; tetraethylene pentamine; di-(1,3-propylene) triamine; N,N-di-(2-aminoethyl) ethylene diamine; and N dodecyl-1,3-propane diamine.

28. The process of claim 21, wherein said polyamine is selected from the group consisting alicyclic diamines, imidazolines, morpholines, and N-aminoalkyl piperazines of the general formula:

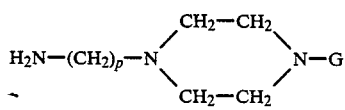

wherein G is independently selected from the group consisting of hydrogen and omega-(nontertiary)aminoalkylene radicals of from 1 to 3 carbon atoms, and p is a number of from 1 to 4.

29. The process of claim 21, wherein said polyamine is a mixture of poly (ethyleneamines) averaging about 5 to about 7 nitrogen atoms per molecule.

30. The process of claim 21, wherein said polyamine is a polyoxyalkylene polyamine having the formula:

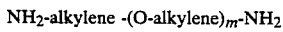

wherein m has a value of about 3 to 70; or

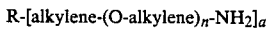

wherein n has a value of about 1 to 40 with the provision that the sum of all the n's is from about 3 to about 70, R is a substituted saturated hydrocarbon radical of up to 10 carbon atoms, wherein the number of substituents on the R group is represented by the value of "a", which is a number from 3 to 6.

31. The process of claim 21, wherein said $C_5$–$C_9$ lactone is reacted with an amino alcohol.

32. The process of claim 31, wherein said amino alcohol is a 2,2-disubstituted-2-amino-1-alkanol of the formula

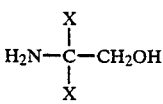

wherein X is alkyl or hydroxyalkyl group with the alkyl groups having from 1 to 3 carbon atoms, wherein at least one of the X substituents is a hydroxyalkyl group of the formula $(CH_2)_nOH$, and wherein n is 1 to 3.

33. The process of claim 32, wherein said amino alcohol tris (hydroxymethyl) amino methane.

34. An oleaginous composition comprising (I) a lubricating oil and (II) a $C_5$–$C_9$ lactone adduct material, said adduct material being prepared by reacting (i) a $C_5$–$C_9$ lactone with (ii) a member selected from the group consisting of (a) a polyamine having from about 2 to about 60 total carbon atoms and from about 2 to about 12 nitrogen atoms, (b) an amino alcohol containing up to about 50 total carbon atoms, from 1 to about five nitrogen atoms and from 1 to about 15 hydroxyl groups, and (c) mixtures of (a) and (b) to form an intermediate lactone adduct, and then reacting said intermediate lactone adduct with (iii) an aliphatic hydrocarbyl saturated or unsaturated, natural or synthetic, straight chain or branched chain monocarboxylic or dicarboxylic acylating agent having from about 12 to about 165 total carbon atoms and at least about twelve carbon atoms in said straight or branched chain to insure that the resulting lactone adduct material is hydrocarbon soluble.

35. The oleaginous composition of claim 34, wherein said acylating agent is a member selected from the group of long chain fatty acids or dimers thereof and hydrocarbyl substituted $C_4$–$C_{10}$ monounsaturated dicarboxylic acid materials, wherein said hydrocarbyl group contains from about twelve to about eighteen carbon atoms.

36. The oleaginous composition of claim 35, wherein said lactone is E-caprolactone.

37. The oleaginous composition of claim 36, where said acylating agent is selected from the group consisting of isostearic acid, stearic acid, linoleic acid, oleic acid, dimers of said acids and octadecenyl succinic anhydride.

38. The oleaginous composition of claim 34, wherein said $C_5$–$C_9$ lactone is reacted with a polyamine, and wherein said polyamine is an aliphatic saturated amine having the formula:

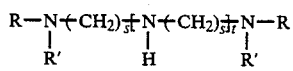

wherein R and R' independently are selected from the group consisting of hydrogen; $C_1$ to $C_{25}$ straight or branched chain alkyl radicals; $C_1$ to $C_{12}$ alkoxy $C_2$ to $C_6$ alkylene radicals; and $C_1$ to $C_{12}$ alkylamino $C_2$ to $C_6$ alkylene radicals; each s is the same or a different number of from 2 to 6, and t is a number of from 0 to 10, with the provision that when t=0, at least one of R or R' must be H such that there are at least two of either primary or secondary amino groups.

39. The oleaginous composition of claim 34, wherein said polyamine is selected from the group consisting of 1,2-diaminoethane; 1,3-diaminopropane; 1,4-diaminobutane; 1,6-diaminohexane; diethylene triamine; triethylene tetramine; tetraethylene pentamine; 1,2-propylene diamine: di-(1,2-propylene)triamine; di-(1,3-propylene) triamine; N,N-dimethyl-1,3-diaminopropane; N,N-di-(2-aminoethyl) ethylene diamine; and N-dodecyl-1,3-propane diamine.

40. The oleaginous composition of claim 34, wherein said polyamine is selected from the group consisting of alicyclic diamines, imidazolines, morpholines and N-aminoalkyl piperazines of the general formula:

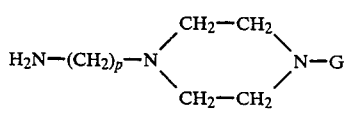

wherein G is independently selected from the group consisting of hydrogen and omega-(nontertiary)aminoalkylene radicals of from 1 to 3 carbon atoms, and p is a number of from 1 to 4.

41. The oleaginous composition of claim 34, wherein said polyamine is a mixture of poly (ethyleneamines) averaging about 5 to about 7 nitrogen atoms per molecule.

42. The oleaginous composition of claim 34, wherein said polyamine is a polyoxyalkylene polyamine having the formula:

NH₂-alkylene-(O-alkylene)ₘ-NH₂ wherein m has a value of about 3 to 70; or

R-[alkylene-(O-alkylene)ₙ-NH₂]ₐ wherein n has a value of about 1 to 40 with the provision that the sum of all the n's is from about 3 to about 70, R is a substituted saturated hydrocarbon radical of up to 10 carbon atoms, wherein the number of substituents on the R group is represented by the value of "a", which is a number from 3 to 6.

43. The oleaginous composition of claim 46, wherein said C₅-C₉ lactone is reacted with an amino alcohol.

44. The oleaginous composition of claim 43, wherein said amino alcohol is a 2,2-disubstituted-2-amino-1-alkanol of the formula $$H_2N-\underset{\underset{X}{|}}{\overset{\overset{X}{|}}{C}}-CH_2OH$$

wherein X is alkyl or hydroxyalkyl group with the alkyl groups having from 1 to 3 carbon atoms, wherein at least one of the X substituents is a hydroxyalkyl group of the formula —(CH₂)ₙOH, and wherein n is 1 to 3.

45. The oleaginous composition of claim 44, wherein said amino alcohol is tris (hydroxymethyl) amino methane.

46. The oleaginous composition of claim 34, wherein said oleaginous material is lubricating oil.

47. A lubricating oil composition comprising lubricating oil and about 0.01 to 15 wt. % of the C₅-C₉ lactone adduct material of claim 3.

48. A lubricating oil comprising a major amount of lubricating oil and about 0.1 to 10 wt. % of the C₅-C₉ lactone adduct material of claim 3.

49. A lubricating oil comprising a major amount of lubricating oil and about 0.01 to 15 wt. % of the C₅-C₉ lactone adduct material of claim 4.

50. A lubricating oil comprising a major amount of lubricating oil and about 0.1 to 10 wt. % of the C₅-C₉ lactone adduct material of claim 16.

51. A lubricating oil comprising a major amount of lubricating oil and about 0.1 to 10 wt. % of the C₅-C₉ lactone adduct material of claim 5.

52. A lubricating oil comprising a major amount of lubricating oil about 0.1 to 10 wt % of the C₅-C₉ lactone adduct material of claim 8.

53. An oil soluble dispersant useful as an oil additive, comprising the product of a reaction mixture comprising:
(I) an aliphatic hydrocarbyl saturated or unsaturated, natural or synthetic, straight chain or branched chain monocarboxylic or dicarboxylic acylating agent having from about 1 to about 165 total carbon atoms; and
(II) a C₅-C₉ lactone adduct formed by reacting (a) a C₅-C₉ lactone with (b) a member selected from the group consisting of (i) a polyamine having from about 2 to 60 total carbon atoms and from about 2 to about 12 nitrogen atoms,
(ii) an amino alcohol containing up to about 50 total carbon atoms, from 1 to about five nitrogen atoms and from 1 to about 15 hydroxyl groups, or mixtures of (i) and (ii),
wherein there are from 1 to about 10 C₅-C₉ lactone derived moieties per unit of said adduct (II) used in the reaction.

54. An oil soluble dispersant according to claim 53, wherein said C₅-C₉ lactone is caprolactone.

55. An oil soluble dispersant according to claim 54, wherein said caprolactone is reacted with a polyamine.

56. An oil soluble despersant according to claim 55, wherein said polyamine is an aliphatic saturated amine having the general formula $$R-\underset{\underset{R'}{|}}{N}+CH_2)_{\overline{s}}\underset{\underset{H}{|}}{N}+CH_2)_{\overline{s}\overline{t}}\underset{\underset{R'}{|}}{N}-R$$

wherein R and R' independently are selected from the group consisting of hydrogen; C₁ to C₂₅ straight of branched chain alkyl radicals; C¹ to C₁₂ alkoxy C₂ to C₆ alkylene radicals; and C₁ to C₁₂ alkylamino C₂ to C₆ alkylene radicals; each s is the same or a different number of from 2 to 6, and t is a number of from 0 to 10, with the provision that when t=0, at least one of R or R' must be H such that there are at least two of either primary of secondary amino groups.

57. An oil soluble dispersant according to claim 56, wherein said polyamine is selected from the group consisting of 1,2-diaminoethane: 1,3-diaminopropane; 1,4-diaminobutane; 1,6-diaminohexane; diethylene triamine; triethylene tetramine; tetraethylene pentamine; 1,2-propylene diamine; di(1,2-propylene)triamine; di-(1,3-propylene) triamine; N,N-dimethyl-1,3-diaminopropane; N,N-di-(2-aminoethyl) ethylene diamine; and N-dodecyl-1,3-propane diamine.

58. The oil soluble dispersant of claim 55, wherein said polyamine is selected from the group consisting of alicyclic diamines, imidazoles, morpholines, and N-aminoalkyl piperazines of the general formula:

$$H_2N-(CH_2)_p-N\underset{CH_2-CH_2}{\overset{CH_2-CH_2}{<}}N-G$$

wherein G is independently selected from the group consisting of hydrogen and omega-(nontertiary)aminoalkylene radicals of from 1 to 3 carbon atoms, and p is a number of from 1 to 4.

59. The oil soluble dispersant of claim 55, wherein said polyamine is a mixture of poly(ethyleneamines) averaging about 5 to about 7 nitrogen atoms per molecule.

60. An oil soluble dispersant according to claim 55, wherein said polyamine is a polyoxyalkylene polyamine having the formula:

NH₂-alkylene-(-O-alkylene)ₘ—NH₂ where m has a value of about 3 to 70; or

R-[alkylene-(-O-alkylene)ₙ—NH₂]ₐ wherein n has a value of about 1 to 40 with the provision that the sum of all the n's is from about 3 to about 70, R is a substituted saturated hydrocarbon radical of up to 10 carbon atoms, wherein the number of substituents on the R group is represented by the value of "a", which is a number from 3 to 6.

61. An oil soluble dispersant according to claim 54, wherein said caprolactone is reacted with an amino alcohol.

62. An oil soluble dispersant according to claim 61, wherein said amino alcohol is a 2,2-disubstituted-2-amino-1-alkanol of the formula

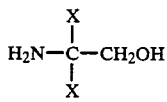

wherein X is a alkyl or hydroxyalkyl group with the alkyl groups having from 1 to 3 carbon atoms, wherein at least one of the X substituents is a hydroxyalkyl group of the formula $-(CH_2)_nOH$, and wherein n is 1 to 3.

63. An oil soluble dispersant according to claim 62, wherein said amino alcohol is tris(hydroxymethyl-)amino methane.

64. An oil soluble reaction product useful as an oil additive of:
(a) an aliphatic hydrocarbyl saturated or unsaturated, natural or synthetic, straight chain or branched chain monocarboxylic or dicarboxylic acylating agent having from about to about 18 total carbon atoms
(b) amine containing 2 to 60 carbon atoms and 2 to 12 nitrogen groups, and,
(c) $C_5$–$C_9$ lactone, wherein (b) is first reacted with (c) and the resulting product is then reacted with (a), and wherein there are about 0.2 to 100 molar proportions of (c) per molar proportion of said reaction product.

65. An oil soluble reaction product according to claim 64 wherein wherein (c) is E-caprolactone, and wherein there are about 0.5 to 20 molar proportions of (c) per molar proportion of said reaction product.

66. An oil soluble reaction product useful as an oil additive of:
(a) an aliphatic hydrocarbyl saturated or unsaturated, natural or synthetic, straight chain or branched chain monocarboxylic or dicarboxylic acylating agent having from about 12 to about 18 total carbon atoms
(b) amino alcohol containing up to about 50 total carbon atoms, from 1 to about 5 nitrogen atoms and from 1 to about 15 hydroxyl groups, and
(c) $C_5$–$C_9$ lactone,
wherein (b) is first reacted with (c) and the resulting product is then reacted with (a), and wherein there are about 0.2 to 100 molar proportions of (c) per molar proportion of said reaction product.

67. An oil soluble reaction product according to claim 66 wherein (c) is E-caprolactone, and wherein there are about 1 to 5 molar proparations of (c) per molar proportion of said reaction product.

68. A lubricating oil composition comprising lubricating oil and an oil soluble reaction product useful as an oil additive, said reaction product being the product of reaction of the intermediate product formed by reacting (a) a $C_5$–$C_9$ lactone with (b) at least one member selected from the group consisting of (i) a polyamine having from about 2 to 60 total carbon atoms and from about 2 to about 12 nitrogen atoms an amino alcohol containing up to about 50 total carbon atoms, from 1 to about five nitrogen atoms and from 1 to about 15 hydroxyl groups, wherein there are 0.2 to 100 molar proportions of (b) in said intermediate product, further reacted with (c) an aliphatic hydrocarbyl saturated or unsaturated, natural or synthetic, straight chain or branched chain monocarboxylic or dicarboxylic acylating agent having from about 12 to about 18 total carbon atoms.

69. A lubricating oil composition according to claim 68, wherein (a) is caprolactone, and wherein there are from about one to about five molar proportions of caprolactone per molar proportion of product obtained by the reaction of (a) with (b).

70. A lubricating crankcase motor oil composition for automotive vehicles and trucks comprising a major amount of lubricating oil; from about 0.01 to 15 wt. % of a dispersant formed by reacting an aliphatic hydrocarbyl saturated or unsaturated, natural or synthetic, straight chain or branched chain monocarboxylic or dicarboxylic acylating agent having from about 12 to about 18 total carbon atoms with the reaction product of a $C_5$–$C_9$ lactone and at least one member selected from the group consisting of (a) polyamines having from about 2 to 60 total carbon atoms and from about 2 to about 12 nitrogen atoms, and (b) amino alcohols containing up to about 50 total carbon atoms, from 1 to about five nitrogen atoms and from 1 to about 15 hydroxyl groups, wherein said dispersant has about one to five molar proportion of acylating agent moieties; and about 3 to 25 wt. % of a metal containing detergent additive.

71. A composition according to claim 70, wherein said $C_5$–$C_9$ lactone is caprolactone.

72. A composition according to claim 71, wherein said composition also contains an effective amount of a zinc dihydrocarbyl dithiophosphate.

73. An additive concentrate comprising about 20 to 90 wt. % lubricating oil and 20 to 80 wt. % of a dispersant which is a $C_5$–$C_9$ lactone adduct material formed by first reacting about 0.2 to 100 molar proportions of a $C_5$–$C_9$ lactone per molar proportion of at least one member selected from the group consisting of (a) polyamines having from about 2 to 60 total carbon atoms and from about 2 to 12 nitrogen atoms and (b) amino alcohols containing up to about 50 total carbon atoms, from 1 to about five nitrogen atoms and from 1 to about 15 hydroxyl groups, to from a lactone adduct intermediate, and then reacting said intermediate with an aliphatic hydrocarbyl saturated or unsaturated, natural or synthetic, straight chain or branched chain monocarboxylic or dicarboxylic acylating agent having from about 12 to about 18 total carbon atoms.

74. A concentrate according to claim 73, wherein said $C_5$–$C_9$ lactone is caprolactone and which also contains an effective amount of a viscosity modifier.

75. A concentrate according to claim 74, which also contains an effective amount of a zinc dihydrocarbyl dithiophosphate.

76. An additive concentrate comprising about 20 to 80 wt. % lubricating oil and about 20 to 80 wt. % of an oil soluble reaction product of a caprolactone adduct and an acylating agent selected from the group consisting of long chain fatty acids, long chain fatty acid dimers and hydrocarbyl substituted $C_4$ to $C_{10}$ monounsaturated dicarboxylic acid producing material having from about twelve to about 18 carbon atoms in said hydrocarbyl substituent, said caprolactone adduct being prepared by reacting caprolactone with at least one member selected from the group consisting of (a) polyamines having from about 2 to 60 total carbon atoms and from about 2 to about 12 nitrogen atoms and (b) amino alcohols containing up to about 50 total carbon atoms, from 1 to about five nitrogen atoms and from 1 to about 15 hydroxyl groups.

77. An additive concentrate according to claim 76, wherein said hydrocarbyl substituted $C_4$ to $C_{10}$ acid producing material is octadecenyl succinic anhydride.

78. An additive concentrate according to claim 76, wherein said long chain fatty acids and said long chain fatty acid dimers are selected from the group consisting of isostearic acid, stearic acid, linoleic acid, oleic acid and dimers thereof.

* * * * *